United States Patent
Cabiri et al.

(10) Patent No.: US 9,744,297 B2
(45) Date of Patent: Aug. 29, 2017

(54) NEEDLE CANNULA POSITION AS AN INPUT TO OPERATIONAL CONTROL OF AN INJECTION DEVICE

(71) Applicant: MEDIMOP Medical Projects Ltd., Ra'anana (IL)

(72) Inventors: Oz Cabiri, Macabim-Reut (IL); Ran Hezkiahu, Herzliya (IL)

(73) Assignee: MEDIMOP MEDICAL PROJECTS LTD., Ra'anana (IL)

( * ) Notice: Subject to any disclaimer, the term of this patent is extended or adjusted under 35 U.S.C. 154(b) by 94 days.

(21) Appl. No.: 14/683,253

(22) Filed: Apr. 10, 2015

(65) Prior Publication Data

US 2016/0296699 A1  Oct. 13, 2016

(51) Int. Cl.
| | | |
|---|---|---|
| A61M 5/20 | (2006.01) | |
| A61M 5/32 | (2006.01) | |
| A61M 5/50 | (2006.01) | |
| A61M 5/162 | (2006.01) | |
| A61M 5/172 | (2006.01) | |
| G06F 19/00 | (2011.01) | |

(52) U.S. Cl.
CPC .......... *A61M 5/1626* (2013.01); *A61M 5/172* (2013.01); *A61M 5/2066* (2013.01); *A61M 5/3202* (2013.01); *A61M 5/3204* (2013.01); *A61M 5/326* (2013.01); *A61M 5/50* (2013.01); *A61M 5/5086* (2013.01); *A61M 2005/2013* (2013.01); *G06F 19/3468* (2013.01)

(58) Field of Classification Search
CPC .... A61M 5/14248; A61M 2005/14252; A61M 5/20; A61M 5/1626; A61M 5/3202; A61M 2005/2013; A61M 5/172; A61M 5/3204; A61M 5/326; A61M 5/50; A61M 5/5086; H01H 1/5805; H01H 2/22; G06F 19/3468

See application file for complete search history.

(56) References Cited

U.S. PATENT DOCUMENTS

| | | | |
|---|---|---|---|
| 3,946,732 A | 3/1976 | Hurscham | |
| 3,994,295 A | 11/1976 | Wulff | |
| 4,167,663 A | 9/1979 | Granzow, Jr. et al. | |
| 4,273,122 A | 6/1981 | Whitney et al. | |
| 4,396,385 A | 8/1983 | Kelly et al. | |

(Continued)

FOREIGN PATENT DOCUMENTS

| | | |
|---|---|---|
| CN | 101868273 A | 10/2010 |
| EP | 0401179 A1 | 12/1990 |

(Continued)

OTHER PUBLICATIONS

U.S. Appl. No. 13/429,942 by Cabiri, filed Mar. 26, 2012.

(Continued)

*Primary Examiner* — Quynh-Nhu H Vu
(74) *Attorney, Agent, or Firm* — Panitch Schwarze Belisario & Nadel LLP

(57) ABSTRACT

A method is disclosed for state sensing and controlling of a multi-state drug delivery device. In some embodiments a power switch is reused as a state sensor. Optionally the state sensor may be toggled by user actions and/or the movements of parts of the device, for example needle and/or a protective element. Optionally, drug discharge and/or status indication is controlled in accordance with sensor output. In some embodiments control is by means of a processor. Alternatively or additionally, control is by means of simple physical circuits.

4 Claims, 16 Drawing Sheets

(56) References Cited

U.S. PATENT DOCUMENTS

| | | |
|---|---|---|
| 4,601,702 A | 7/1986 | Hudson |
| 4,634,426 A | 1/1987 | Kamen |
| 4,886,499 A | 12/1989 | Cirelli et al. |
| 4,908,014 A | 3/1990 | Kroyer |
| 4,919,596 A | 4/1990 | Slate et al. |
| 4,950,235 A | 8/1990 | Slate et al. |
| 4,950,246 A | 8/1990 | Muller |
| 5,109,850 A | 5/1992 | Blanco et al. |
| 5,131,816 A | 7/1992 | Brown et al. |
| 5,254,096 A | 10/1993 | Rondelet et al. |
| 5,342,313 A | 8/1994 | Campbell et al. |
| 5,354,287 A | 10/1994 | Wacks |
| 5,383,865 A | 1/1995 | Michel |
| 5,411,482 A | 5/1995 | Campbell |
| 5,501,665 A | 3/1996 | Jhuboo et al. |
| 5,558,639 A | 9/1996 | Gangemi |
| 5,593,390 A | 1/1997 | Castellano et al. |
| 5,616,132 A | 4/1997 | Newman |
| 5,643,218 A | 7/1997 | Lynn et al. |
| 5,647,853 A | 7/1997 | Feldmann et al. |
| 5,658,133 A | 8/1997 | Anderson et al. |
| 5,690,618 A | 11/1997 | Smith et al. |
| D393,314 S | 4/1998 | Meisner et al. |
| 5,800,420 A | 9/1998 | Gross et al. |
| 5,807,375 A | 9/1998 | Gross et al. |
| 5,814,020 A | 9/1998 | Gross |
| 5,851,197 A | 12/1998 | Marano et al. |
| 5,858,001 A | 1/1999 | Tsals et al. |
| 5,858,008 A | 1/1999 | Capaccio |
| 5,931,814 A | 8/1999 | Alex et al. |
| 5,957,895 A | 9/1999 | Sage et al. |
| 5,993,423 A | 11/1999 | Choi |
| 5,997,501 A | 12/1999 | Gross et al. |
| 6,004,297 A | 12/1999 | Steenfeldt-Jensen et al. |
| 6,064,797 A | 5/2000 | Crittendon et al. |
| 6,074,369 A | 6/2000 | Sage et al. |
| 6,175,688 B1 | 1/2001 | Cassidy et al. |
| 6,186,982 B1 | 2/2001 | Gross et al. |
| 6,200,289 B1 | 3/2001 | Hochman et al. |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,362,591 B1 | 3/2002 | Moberg |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,517,517 B1 | 2/2003 | Farrugia et al. |
| D471,274 S | 3/2003 | Diaz et al. |
| D471,983 S | 3/2003 | Hippolyte et al. |
| 6,530,901 B1 | 3/2003 | Tsukada et al. |
| 6,555,986 B2 | 4/2003 | Moberg |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,699,218 B2 | 3/2004 | Flaherty et al. |
| 6,749,587 B2 | 6/2004 | Flaherty |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,950,028 B2 | 9/2005 | Zweig |
| 6,960,192 B1 | 11/2005 | Flaherty et al. |
| 7,001,360 B2 | 2/2006 | Veasey et al. |
| 7,048,715 B2 | 5/2006 | Diaz et al. |
| 7,060,059 B2 | 6/2006 | Keith et al. |
| 7,128,727 B2 | 10/2006 | Flaherty et al. |
| 7,144,384 B2 | 12/2006 | Gorman et al. |
| 7,193,521 B2 | 3/2007 | Moberg et al. |
| D544,092 S | 6/2007 | Lewis |
| 7,247,149 B2 | 7/2007 | Beyerlein |
| 7,250,037 B2 | 7/2007 | Shermer et al. |
| 7,267,669 B2 | 9/2007 | Staunton et al. |
| 7,303,549 B2 | 12/2007 | Flaherty et al. |
| 7,390,314 B2 | 6/2008 | Stutz, Jr. et al. |
| 7,407,493 B2 | 8/2008 | Cane' |
| 7,455,663 B2 | 11/2008 | Bikovsky |
| 7,465,290 B2 | 12/2008 | Reilly |
| 7,497,842 B2 | 3/2009 | Diaz et al. |
| 7,524,304 B2 | 4/2009 | Genosar |
| 7,530,964 B2 | 5/2009 | Lavi et al. |
| 7,547,281 B2 | 6/2009 | Hayes et al. |
| 7,563,253 B2 | 7/2009 | Tanner et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| D602,155 S | 10/2009 | Foley et al. |
| D602,586 S | 10/2009 | Foley et al. |
| D604,835 S | 11/2009 | Conley |
| 7,621,893 B2 | 11/2009 | Moberg et al. |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,227 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,753,879 B2 | 7/2010 | Mernoe |
| 7,766,873 B2 | 8/2010 | Moberg et al. |
| 7,776,030 B2 | 8/2010 | Estes et al. |
| 7,780,636 B2 | 8/2010 | Radmer et al. |
| 7,780,637 B2 | 8/2010 | Jerde et al. |
| 7,789,857 B2 | 9/2010 | Moberg et al. |
| 7,789,862 B2 | 9/2010 | Thorne, Jr. |
| 7,801,599 B2 | 9/2010 | Young et al. |
| 7,806,868 B2 | 10/2010 | De Polo et al. |
| 7,815,622 B2 | 10/2010 | Istoc et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,857,131 B2 | 12/2010 | Vedrine |
| 7,879,025 B2 | 2/2011 | Jacobson et al. |
| 7,879,026 B2 | 2/2011 | Estes et al. |
| 7,892,206 B2 | 2/2011 | Moberg et al. |
| 7,918,825 B2 | 4/2011 | O'Connor et al. |
| 7,918,843 B2 | 4/2011 | Genosar et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |

(56) References Cited

U.S. PATENT DOCUMENTS

| | | |
|---|---|---|
| 7,967,784 B2 | 6/2011 | Pongpairochana et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,436 B2 | 11/2011 | Causey et al. |
| 8,062,253 B2 | 11/2011 | Nielsen et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,923 B2 | 4/2012 | Adams et al. |
| 8,167,841 B2 | 5/2012 | Teisen-Simony et al. |
| 8,172,804 B2 | 5/2012 | Bikovsky |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,267,893 B2 | 9/2012 | Moberg et al. |
| 8,267,921 B2 | 9/2012 | Yodfat et al. |
| 8,287,520 B2 | 10/2012 | Drew et al. |
| 8,308,679 B2 | 11/2012 | Hanson et al. |
| 8,348,898 B2 | 1/2013 | Cabiri |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,495,918 B2 | 7/2013 | Bazargan et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,574,216 B2 | 11/2013 | Istoc et al. |
| 8,603,026 B2 | 12/2013 | Favreau |
| 8,603,027 B2 | 12/2013 | Favreau |
| 8,617,110 B2 | 12/2013 | Moberg et al. |
| 8,628,510 B2 | 1/2014 | Bazargan et al. |
| 8,647,074 B2 | 2/2014 | Moberg et al. |
| 8,647,296 B2 | 2/2014 | Moberg et al. |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,810,394 B2 | 8/2014 | Kalpin |
| 9,463,280 B2 | 10/2016 | Cabiri |
| 2002/0040208 A1 | 4/2002 | Flaherty et al. |
| 2002/0043951 A1 | 4/2002 | Moberg |
| 2002/0055711 A1 | 5/2002 | Lavi et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0199825 A1 | 10/2003 | Flaherty |
| 2004/0085215 A1 | 5/2004 | Moberg et al. |
| 2004/0092873 A1 | 5/2004 | Moberg |
| 2004/0116866 A1 | 6/2004 | Gorman et al. |
| 2004/0260233 A1 | 12/2004 | Garibotto et al. |
| 2005/0065472 A1 | 3/2005 | Cindrich et al. |
| 2005/0070845 A1 | 3/2005 | Faries et al. |
| 2005/0071487 A1 | 3/2005 | Lu et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0238507 A1 | 10/2005 | Dilanni et al. |
| 2006/0095014 A1 | 5/2006 | Ethelfeld |
| 2006/0122577 A1 | 6/2006 | Poulsen et al. |
| 2006/0173408 A1 | 8/2006 | Wyrick |
| 2006/0173439 A1 | 8/2006 | Thorne et al. |
| 2006/0184154 A1 | 8/2006 | Moberg et al. |
| 2006/0229569 A1 | 10/2006 | Lavi et al. |
| 2006/0264890 A1 | 11/2006 | Moberg et al. |
| 2006/0283465 A1 | 12/2006 | Nickel et al. |
| 2007/0021733 A1 | 1/2007 | Hansen et al. |
| 2007/0049865 A1 | 3/2007 | Radmer et al. |
| 2007/0118405 A1 | 5/2007 | Campbell et al. |
| 2007/0149926 A1 | 6/2007 | Moberg et al. |
| 2007/0167912 A1 | 7/2007 | Causey et al. |
| 2007/0191770 A1 | 8/2007 | Moberg et al. |
| 2007/0219480 A1 | 9/2007 | Kamen et al. |
| 2007/0282269 A1 | 12/2007 | Carter et al. |
| 2008/0033369 A1 | 2/2008 | Kohlbrenner et al. |
| 2008/0051710 A1 | 2/2008 | Moberg et al. |
| 2008/0051711 A1 | 2/2008 | Mounce et al. |
| 2008/0051727 A1 | 2/2008 | Moberg et al. |
| 2008/0059133 A1 | 3/2008 | Edwards et al. |
| 2008/0125700 A1 | 5/2008 | Moberg et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0156476 A1 | 7/2008 | Smisson et al. |
| 2008/0167641 A1 | 7/2008 | Hansen et al. |
| 2008/0188813 A1 | 8/2008 | Miller et al. |
| 2008/0215006 A1 | 9/2008 | Thorkild |
| 2008/0221522 A1 | 9/2008 | Moberg et al. |
| 2008/0221523 A1 | 9/2008 | Moberg et al. |
| 2008/0269723 A1 | 10/2008 | Mastrototaro et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0054750 A1 | 2/2009 | Jennewine |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0124977 A1 | 5/2009 | Jensen |
| 2009/0149830 A1 | 6/2009 | Spector |
| 2009/0182277 A1 | 7/2009 | Carter |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0299397 A1 | 12/2009 | Ruan et al. |

(56) References Cited

U.S. PATENT DOCUMENTS

| | | |
|---|---|---|
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0037680 A1 | 2/2010 | Moberg et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0145303 A1 | 6/2010 | Yodfat et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0217192 A1 | 8/2010 | Moberg et al. |
| 2010/0217193 A1 | 8/2010 | Moberg et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0276411 A1 | 11/2010 | Hansen et al. |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0060284 A1 | 3/2011 | Harr |
| 2011/0119033 A1 | 5/2011 | Moberg et al. |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0178472 A1 | 7/2011 | Cabiri |
| 2011/0184342 A1 | 7/2011 | Pesach et al. |
| 2011/0201998 A1 | 8/2011 | Pongpairochana et al. |
| 2011/0224614 A1 | 9/2011 | Moberg et al. |
| 2011/0238031 A1 | 9/2011 | Adair et al. |
| 2011/0245773 A1 | 10/2011 | Estes et al. |
| 2011/0264383 A1 | 10/2011 | Moberg et al. |
| 2011/0270160 A1 | 11/2011 | Mernoe |
| 2011/0282282 A1 | 11/2011 | Lorenzen et al. |
| 2011/0295205 A1 | 12/2011 | Kaufmann et al. |
| 2011/0313238 A1 | 12/2011 | Reichenbach et al. |
| 2011/0313351 A1 | 12/2011 | Kamen et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022499 A1 | 1/2012 | Anderson et al. |
| 2012/0025995 A1 | 2/2012 | Moberg et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041370 A1 | 2/2012 | Moberg et al. |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete, Jr. et al. |
| 2012/0310153 A1 | 12/2012 | Moberg et al. |
| 2013/0068319 A1 | 3/2013 | Plumptre et al. |
| 2013/0096509 A1 | 4/2013 | Avery et al. |
| 2013/0133438 A1 | 5/2013 | Kow et al. |
| 2013/0175192 A1* | 7/2013 | Iio .......................... A61M 5/003 206/438 |
| 2013/0218089 A1 | 8/2013 | Davies et al. |
| 2013/0218092 A1 | 8/2013 | Davies et al. |
| 2013/0237953 A1 | 9/2013 | Kow et al. |
| 2013/0245595 A1 | 9/2013 | Kow et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253472 A1 | 9/2013 | Cabiri |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0171881 A1* | 6/2014 | Cabiri ............... A61M 5/14248 604/263 |
| 2014/0194819 A1 | 7/2014 | Maule et al. |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0210631 A1* | 7/2014 | Zavis ....................... G01R 5/28 340/815.45 |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |
| 2014/0288511 A1 | 9/2014 | Tan-Malecki et al. |
| 2014/0330240 A1 | 11/2014 | Cabiri et al. |
| 2015/0011965 A1 | 1/2015 | Cabiri |
| 2015/0011976 A1 | 1/2015 | Vouillamoz et al. |
| 2015/0032084 A1 | 1/2015 | Cabiri |
| 2015/0119797 A1 | 4/2015 | Cabiri |
| 2015/0224253 A1 | 8/2015 | Cabiri |
| 2016/0015910 A1* | 1/2016 | Mukai ..................... A61M 5/20 206/365 |

FOREIGN PATENT DOCUMENTS

| | | |
|---|---|---|
| EP | 0744975 A1 | 12/1996 |
| EP | 1666080 A1 | 6/2006 |
| EP | 2060606 A1 | 5/2009 |
| EP | 2345441 A1 | 7/2011 |
| EP | 2454483 B1 | 8/2015 |
| WO | 8911302 A1 | 11/1989 |
| WO | 9009202 A1 | 8/1990 |
| WO | 9521645 A1 | 8/1995 |
| WO | 9632975 A1 | 10/1996 |
| WO | 9721457 A1 | 6/1997 |
| WO | 9733638 A1 | 9/1997 |
| WO | 2007092618 A2 | 8/2007 |
| WO | 2007130868 A1 | 11/2007 |
| WO | 2008024810 A2 | 2/2008 |
| WO | 2008024814 A2 | 2/2008 |
| WO | 2008129549 A1 | 10/2008 |
| WO | 2009081262 A1 | 7/2009 |
| WO | 2011090955 A1 | 7/2011 |
| WO | 2011113806 A1 | 9/2011 |
| WO | 2013115843 A1 | 8/2013 |
| WO | 2013148270 A2 | 10/2013 |
| WO | 2014179210 A1 | 11/2014 |

OTHER PUBLICATIONS

U.S. Appl. No. 13/886,867 by Cabiri, filed May 3, 2013.
Int'l Search Report and Written Opinion issued Apr. 5, 2013 in Int'l Application No. PCT/US2012/050696.

(56) References Cited

OTHER PUBLICATIONS

Office Action issued Aug. 15, 2013 in U.S. Appl. No. 13/429,942 by Cabiri.
Office Action issued Jan. 16, 2014 in U.S. Appl. No. 13/429,942 by Cabiri.
Int'l Search Report and Written Opinion issued Jun. 30, 2014 in Int'l Application No. PCT/US2013/031598.
Int'l Search Report and Written Opinion issued Aug. 28, 2014 in Int'l Application No. PCT/US2014/035662.
Int'l Preliminary Report on Patentability issued Aug. 14, 2014 in Int'l Application No. PCT/US2012/050696.
U.S. Appl. No. 14/372,384 by Cabiri, filed Jul. 15, 2014.
Office Action issued Jan. 28, 2015 in U.S. Appl. No. 13/429,942 by Cabiri.
U.S. Appl. No. 14/593,041 by Cabiri, filed Jan. 9, 2015.
Office Action issued Nov. 25, 2015 in U.S. Appl. No. 14/372,384 by Cabiri.
Office Action issued Oct. 28, 2015 in U.S. Appl. No. 13/429,942 by Cabiri.
Office Action issued Jan. 5, 2016 in U.S. Appl. No. 14/696,644 by Cabiri.
Office Action issued Dec. 3, 2015 in CN Application No. 201280068544.0.
Office Action issued Feb. 24, 2016 in U.S. Appl. No. 13/429,942 by Cabiri.
Office Action issued May 18, 2015 in U.S. Appl. No. 13/429,942 by Cabiri.
Int'l Preliminary Report on Patentability issued Oct. 9, 2014 in Int'l Application No. PCT/US13/31598.
Int'l Preliminary Report on Patentability issued Nov. 12, 2015 in Int'l Application No. PCT/US14/35662.
Office Action issued Apr. 19, 2016 in U.S. Appl. No. 14/372,384, by Cabiri.
Office Action issued May 17, 2016 in U.S. Appl. No. 13/886,867, by Cabiri.
Office Action issued Jun. 1, 2016 in CN Application No. 2013800274556.
Office Action issued Jun. 17, 2016 in CN Application No. 201280068544.0.
Office Action issued Jul. 29, 2016 in U.S. Appl. No. 14/696,644, by Cabiri.

\* cited by examiner

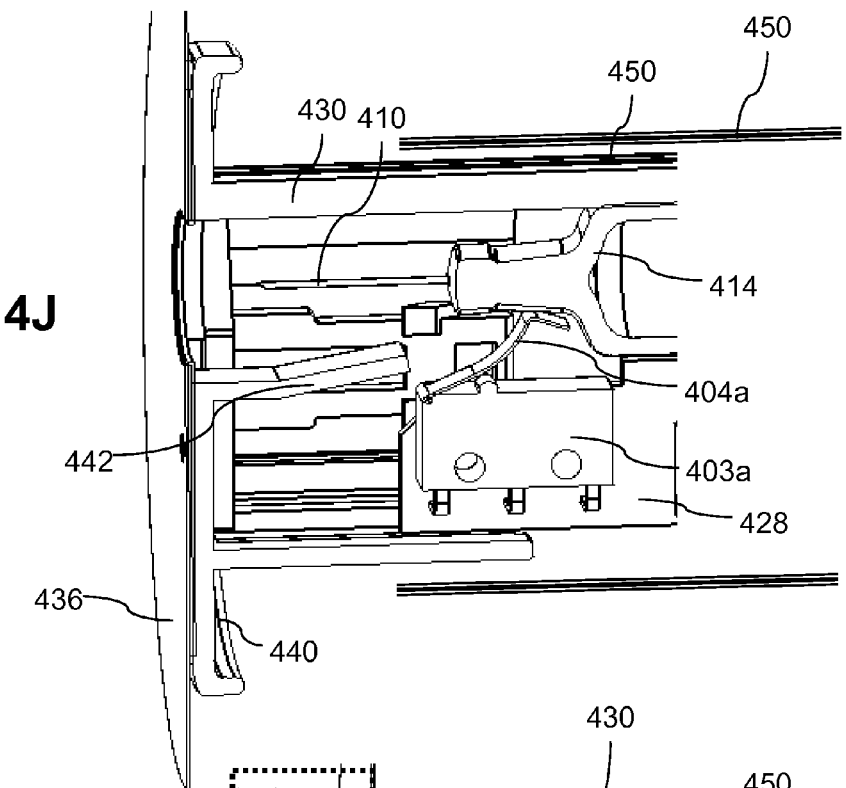
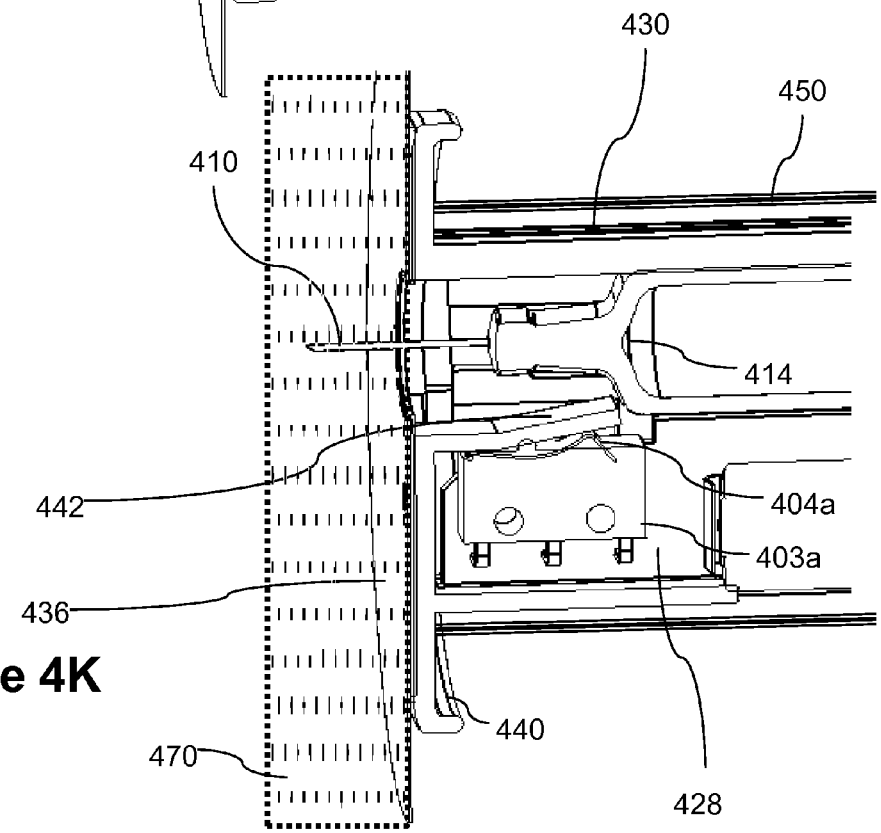

NEEDLE CANNULA POSITION AS AN INPUT TO OPERATIONAL CONTROL OF AN INJECTION DEVICE

BACKGROUND OF THE INVENTION

The present invention, in some embodiments thereof, relates to a control system for a drug delivery device, more particularly, but not exclusively, to a system to sense the stages of operation of an autoinjector.

U.S. Patent Application Publication no. 2014/0207080 to Allerdings "relates to a method and to a monitoring device for monitoring operation of a drug delivery device, the monitoring device comprising of at least a first and a second sensor arranged at a distance from each other with regard to a first direction and being adapted to generate a first and a second electrical signal in response to an operation of the device, a processing unit configured to determine a time delay between the first and the second electrical signals and being adapted to determine at least one state parameter of the drug delivery device on the basis of said time delay."

U.S. Patent Application Publication no. 2014/0171881 to the present inventor discloses, "a method of preparing a compound device for use. The device may include a sealed component and an active outer surface. The outer surface may be protected by a surface cover. Preparing the device may include activating the active outer surface by removing the surface cover and exposing an internal portion of the sealed component to the exterior of the device by unsealing the sealed component and synchronizing the activating and said unsealing using a coupler attached to the surface cover and the sealed component."

U.S. Patent Application Publication no. 2014/0163526 to the present inventor discloses that, "an automated injection device may be loaded with a standard type syringe and/or hypodermic needle. Optionally the syringe may be supplied loaded with medicine and/or covered with a sterile needle cover. The syringe may be loaded into the injector without breaking the sterility (for example in a sterile environment and/or without removing a sterile needle cover). Injector may include for example a fastener (for example an adhesive base). In some embodiments, the fastener and/or a stabilizer may assist a user to hold injector steady on the skin of a patient for an extended period. For example, injector may be used to give injections of volume ranging between 0.5 and 3.0 ml over a time period ranging between 30 sec to 180 sec."

Additional background art includes International Patent Application Publication no. WO2013173092 to the present inventor.

BRIEF SUMMARY OF THE INVENTION

According to an aspect of some embodiments of the invention, there is provided a method of reusing a power switch as a sensor to indicate multiple stages of operation of a delivery drug delivery device comprising: Providing a device where the power switch interrupts a power supply circuit; toggling of the switch to activate the device; engaging the device to a subject, the engaging causing a further toggling the switch while the device remains activated; initiating discharge of the drug in response to the further toggling of the switch.

According to some embodiments of the invention, during when the power supply is interrupted, substantially no power is consumed by the device.

According to some embodiments of the invention, the action is triggered when the further toggling occurs in a predefined time period after the toggling and wherein an alternative action is triggered if the further toggling occurs previous to the time period.

According to some embodiments of the invention, the action is triggered when a plunger movement is within a predetermined range in a predefined time period and wherein an alternative action is triggered when the plunger movement is outside of the predetermined range in the predetermined time period.

According to some embodiments of the invention, the initiating occurs in response to the further toggling in a predefined time period after the toggling and wherein an alternative action is triggered if the further toggling does not occur within the time period.

According to some embodiments of the invention, the toggling is by removing a protective element from the device, the protective element inhibiting the engaging of the device to a subject.

According to some embodiments of the invention, the method further comprises: disengaging of the device from the subject causing yet another toggling of the switch; indicating to a user of a completion of delivery via a coded output to in response to the yet another toggling of the switch.

According to some embodiments of the invention, the method further comprises: disengaging of the device from the subject causing yet another toggling of the switch; stopping discharge of the drug in response to the yet another toggling.

According to an aspect of some embodiments of the invention, there is provided a method of staged operation of an autoinjector comprising: sensing a change in position of an injection needle; determining a state of the autoinjector in response to the sensing, and indicating the state to a user with a coded output.

According to some embodiments of the invention, the change in position includes inserting the needle past a skin contact surface of the autoinjector into a subject and wherein the coded output indicates that the autoinjector is operating properly.

According to some embodiments of the invention, the method further comprises: removing a protective element from the autoinjector by a user, the removing causing connecting of a power supply circuit thereby activating the autoinjector; further indicating via another coded output to the user a ready state of the device in response to the activating.

According to some embodiments of the invention, the method further comprises: engaging by a user of the device to a subject after the further indicating, and wherein the inserting a needle is a result of the engaging.

According to some embodiments of the invention, the method further comprises: initiating discharging of the drug in response to the sensing of the change in position.

According to some embodiments of the invention, the method further comprises: disengaging of the device in response to a completion of the discharging, the disengaging including retraction of the needle with respect to a skin contact surface.

According to some embodiments of the invention, the method further comprises: sensing the retracting or manual retracting or disconnecting from the skin and signaling via a further coded output to a user the completion of operation of the device, the signaling in response to the sensing of the retracting.

According to an aspect of some embodiments of the invention, there is provided a status sensor assembly for a multi-stage drug delivery device comprising: a first power supply circuit; a processor; a power switch isolating the first power supply circuit from the processor when the device is in an inactive stage and wherein in response to toggling of the power switch when the device is in the inactive stage the power supply circuit is connected to the processor, supplying power to the processor; the processor programmed to initiate an activated stage of the device in response to the supplying of power to the processor; a trigger assembly positioned to re-toggle the power switch upon engagement of the device to a subject; a sensor circuit indicating to the processor the re-toggling of the switch, the processor programmed to switch the device to a discharging stage in response to the indicating of the re-toggling; a driver responsive to the processor, the driver discharging the drug from the device when the device is in the discharge stage.

According to some embodiments of the invention, the assembly further comprises: a second power supply circuit, the second power supply circuit supplying no power to the processor when the device is in the inactive stage, the second power supply circuit responsive to the processor for supplying power to the processor in a discharging stage.

According to some embodiments of the invention, in the inactive stage, substantially no power is supplied to the processor.

According to some embodiments of the invention, the assembly further comprises: a protective element, inhibiting engagement of the device to a subject the protective element connected to the power switch for performing the toggling when the protective element is removed from the device.

A protective element, inhibiting engagement of the device to a subject said protective element connected to said power switch for performing said toggling when said protective element is removed from the device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4M are various views of a two sensor drug delivery device in accordance with an embodiment of the current invention;

DETAILED DESCRIPTION OF THE INVENTION

Overview

Figure 1A:
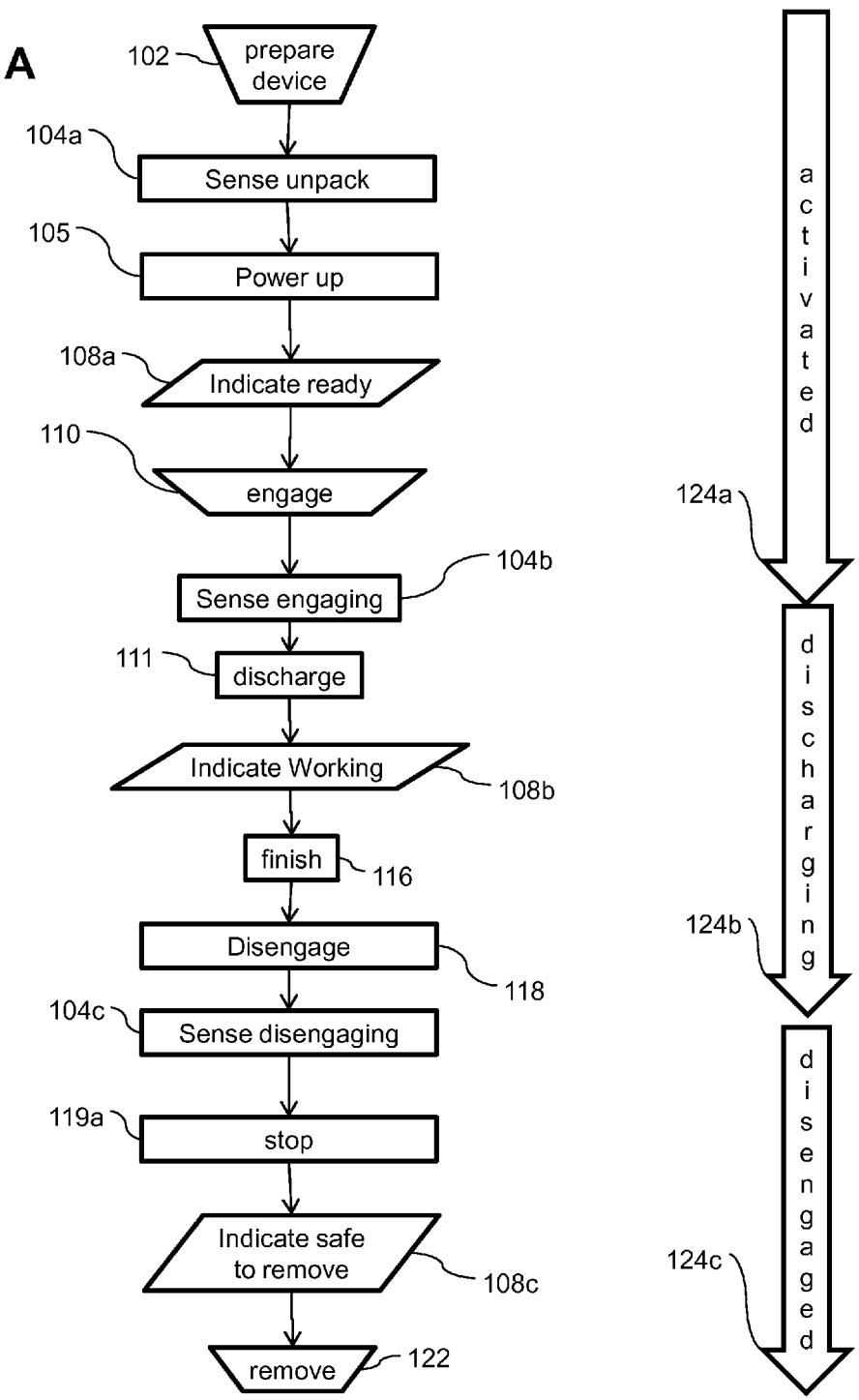
FIGS. 1A and 1B are flow charts illustrations of methods of controlling a drug delivery device in accordance with embodiments of the current invention.

The present invention, in some embodiments thereof, relates to a control system for a drug delivery device, more particularly, but not exclusively, to a system to sense the stages of operation of an autoinjector.

An aspect of some embodiments of the present invention relates to reuse of a power switch to sense stages of operation and/or states of a drug delivery device. In the current disclosure reuse of a power switch as a sensor means using same switch to selectively interrupt power and to act as a sensor by opening/closing a circuit In some embodiments, a power switch may be used to isolate a power supply (for example a battery) of a drug delivery device. For example, before use and/or during storage isolating the power supply may preserve the power supply and/or reduce the risk of producing a spark in an explosive area (for example during sterilization in Ethylene Oxide Chamber). In some embodiments, a user may initially toggle the switch to activate the device before use. In the current disclosure the term toggle when used as a verb means to switch a switch and/or device from one state to another state. A two-way switch may be toggled from a first state to a second state and then toggled from the second state back to the first state. In some embodiments, the switch may be further toggled back and/or forth at further stages of operation and/or at various states of the injector. The order and/or timing of further toggling of the power switch may be used to sense the state of the device and/or control the device. Optionally, once the system has been activated, further toggling of the switch may not deactivate the system and/or may not re-isolate the power supply. For example the system may include an alternative power supply circuit which powers the system once the power supply switch has been toggled initially.

In some embodiments, toggling of the power switch after initial activation of the device may trigger a further action. For example the triggered action may depend on the timing and sequence of the toggling. For example, after the initial toggling, normal operation of the system may cause further toggling of the switch within a predefined time period. If the switch is further toggled in the predefined time period, the device may be switched in the next operational stage and/or an indicator may be communicated to the user that the device is operating properly and/or has progressed to the next stage of operation. If the switch is further toggled previous to the time period and/or is not further toggled during the time period, the device may cease operation and/or lock in a neutralized state and/or warn a user of a fault in operation and/or take a corrective action. In some embodiments locking is irreversible. Optionally locking is reversible. In some embodiments, reversing the locking of the device may be by the user. Alternatively or additionally reversing the locking of the device may require a supervisor and/or a medical professional.

In some embodiments, the initially toggling of the switch may occur when the user un-packages the device and/or removes a safety cover of the device. Optionally, further toggling occurs when the device is engaged to a subject, for example the switch may be toggled by movement of a drug reservoir when injection needle is extended from the device. Optionally, further toggling occurs when the device is disengaged from the subject, for example the switch may be toggled by movement of a drug reservoir when the injection needle is retracted into the device. Optionally the user and the subject may be the same person and/or they may be two different people.

An aspect of some embodiments of the present invention relates to control system for a drug delivery device. Optionally the control system will sense status of the device based on the position of a drug reservoir and/or a protective covering of the device and/or of a needle assembly. The status may be determined by order and/or timing of sensing. Optionally the control system will indicate to a user a status of the device. For example, the system may inform the user that the device is ready for use and/or that the device is working properly and/or that the device is malfunctioning and/or that the device has successfully completed delivery. For example, a user indicator may include a coded indicator.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Methods of Controlling a Multi-Stage Drug Delivery Device

Referring now to the drawings, FIG. 1 is a flow chart illustration of a method of controlling a multi-stage drug delivery device in accordance with an embodiment of the current invention. For example, operation of the device may include three stages of proper delivery, an activated stage 124a and/or a discharging stage 124b and/or a stopped stage 124c. Optionally, the device may enter activated stage 124a when the device senses 104a itself being prepared. Optionally, the device may enter discharging stage 124b when the device senses 104b insertion 110 of a needle. Optionally, the device may enter the stopped stage 124c when the device senses 104c disengaging 118 (for example retraction) of a needle.

In some embodiments, a user may prepare 102 a device. For example, preparing the device may include unpacking the device and/or a manual action following the like removing safety locker and/or needle protector and/or an adhesive cover and/or removing the device from a box. Optionally, preparing 102 the device will activate 105 the device. Optionally, preparing 102 an element that is external and/or that obviously impedes use may activate 105 an element that is internal and/or whose functioning is not obvious to the user. For example, preparing 102 the device may include removing a protective cover (for example a needle cover and/or an adhesive protector). The device may sense 104a removal of the cover. For example, removal of the cover may toggle a sensor (for example a power switch). Toggling the power switch may optionally connect a power supply to an active element of the device activating 105 the device. For example, a processor may be connected to the power supply and/or the processor may activate 105 the other components of the device and/or send a coded signal to an output device. Optionally, upon activation, the output device (for example an LED) may indicate 108a a ready status of the device. For example, the output device may present a coded status indicator. For example, an LED may glow blue, indicating that the device has been activated 105 and/or is ready to be engaged 110. Alternatively or additionally there may be an alternative indicator, for example an audio and/or a tactile indicator such as a noise and/or a vibration.

In some embodiments, when a user recognizes the ready indicator 108a he may engage 110 the device. For example, placing the device on the skin of the subject and/or pushing it against the skin of the subject may engage 110 the device. Alternatively or additionally, engaging 110 may include, pushing a needle into the subject and/or pushing a button. In some embodiments, sensing 104b the engaging may include toggling a sensor by movement of the needle and/or by movement of an associated part of the device (for example a drug reservoir connected to the needle). In some embodiments inserting a needle may include moving of a needle tip that was behind a skin contacting element with respect to the skin contacting element to protrude beyond the skin contacting element. Optionally, inserting a needle may include moving the needle and/or the reservoir with respect to a housing; alternatively or additionally, the housing may collapse (for instance be shortened) such that skin contact surface moves with respect to the needle and/or with respect to another part of the housing exposing the needle.

In some embodiments, when the device senses 104b that it has been engaged 110 to the subject, the device may enter a discharging stage 124b. For example, during discharging stage 124b the drug may be discharged 111 to the subject. Optionally, through the activated stage 124a the drug reservoir may remain in its originally filled state. During the discharge stage 124b, the reservoir optionally goes from the originally filled stage through a partially filled state to a final drained state. In some embodiments the reservoir may be visible to the user to see the state of the drug and/or the fill state of the reservoir (initially filled, partially drained and/or fully drained). In some embodiments, the initially filled reservoir may be filled to capacity. Alternatively or additionally, in the initially filled state, the reservoir may only be partially filled, for example between 90 to 100% and/or between 50 to 90% and/or between 20 to 50% capacity. In some embodiments the reservoir may include more than a single fluid or powder. Optionally distributing the drug includes mixing the materials. In some embodiments the state of the reservoir, for example full, partially full, empty, including separate materials, partially mixed materials and/or fully mixed materials may be visible to the user (for example through a window in the housing of the device).

In some embodiments, during discharge stage 124b, the device may display working indicator 108b. For example, the working indicator may include a blinking green LED. Optionally changing of stages, controlling actuators and/or motors and/or activation of indicators may be controlled by a logic circuit for example a processor. Alternatively or additionally, sensors and/or control logic may be the result of physical devices and/or physical changes and/or physical relationships between parts. For example, a needle movement sensor may include a physical switch. The switch optionally directly connects a motor and/or an indicator to a power supply. Engaging the needle may toggle the switch on and/or turn on an indicator and/or a motor etc.

In some embodiments, when the discharge finishes 116 the device may disengage 118 from the subject. For example, the device may disengage 118 when the reservoir reaches a fully drained state. In the fully drained state the reservoir may be substantially empty. For example, discharge may be driven by a motor pushing a plunger. Discharge 111 optionally continues as long as resistance to movement of the plunger is less than a determined value. When resistance rises (for example due to the plunger reaching the end of the reservoir and/or due to a blockage of the fluid path) a release mechanism optionally causes the plunger and/or reservoir and/or needle to disengage 118. For example disengagement 118 may include retracting the needle and/or reservoir and/or plunger. In some embodiments, discharge 111 may end before the reservoir is empty. For example discharge may end when the reservoir is 90% to 100% and/or between 50 to 90% and/or between 20 to 50% empty.

In some embodiments, disengaging 118 a drug delivery device from a subject may include retracting a needle. For example retracting a needle may include moving the needle with respect to a stationary housing and/or lengthening the housing to cover the tip of the needle.

In some embodiments, the disengaging 118 is sensed 104c by the device. Optionally, the sensed action may be a key outcome of disengaging and/or an action near the end of a causal chain. For example, retraction of the needle may toggle a switch and/or an optical sensor and/or a field sensor (for example a Hall sensor and/or a magnetic sensor). Optionally upon sensing disengagement 118, discharging 111 may be stopped 119a. For example stopping 119a discharging 111 may include stopping 119a a pump and/or an actuator and/or a motor. Alternatively or additionally, stopping 119a may include nullifying a working indicator 108b. Stopping optionally may preserve a power source for reuse. Alternatively or additionally, stopping 119a may include locking the device to prevent restarting. For example locking the device may include setting a flag to prevent reactivation. Optionally, upon sensing disengagement 118 the device may enter disengaged mode 124c. For example in disengaged mode 124c, a safe to remove indicator 108c may be displayed to the user. Once the device is in disengaged stage 124c a user may optionally remove 122 the device. Optionally, a timer and/or indicator may warn the user and/or a supervisor if the device is not removed within a reasonable time period for example ranging between 1 second to 1 min and/or 1 to 3 minutes after injection is completed.

Figure 1B:
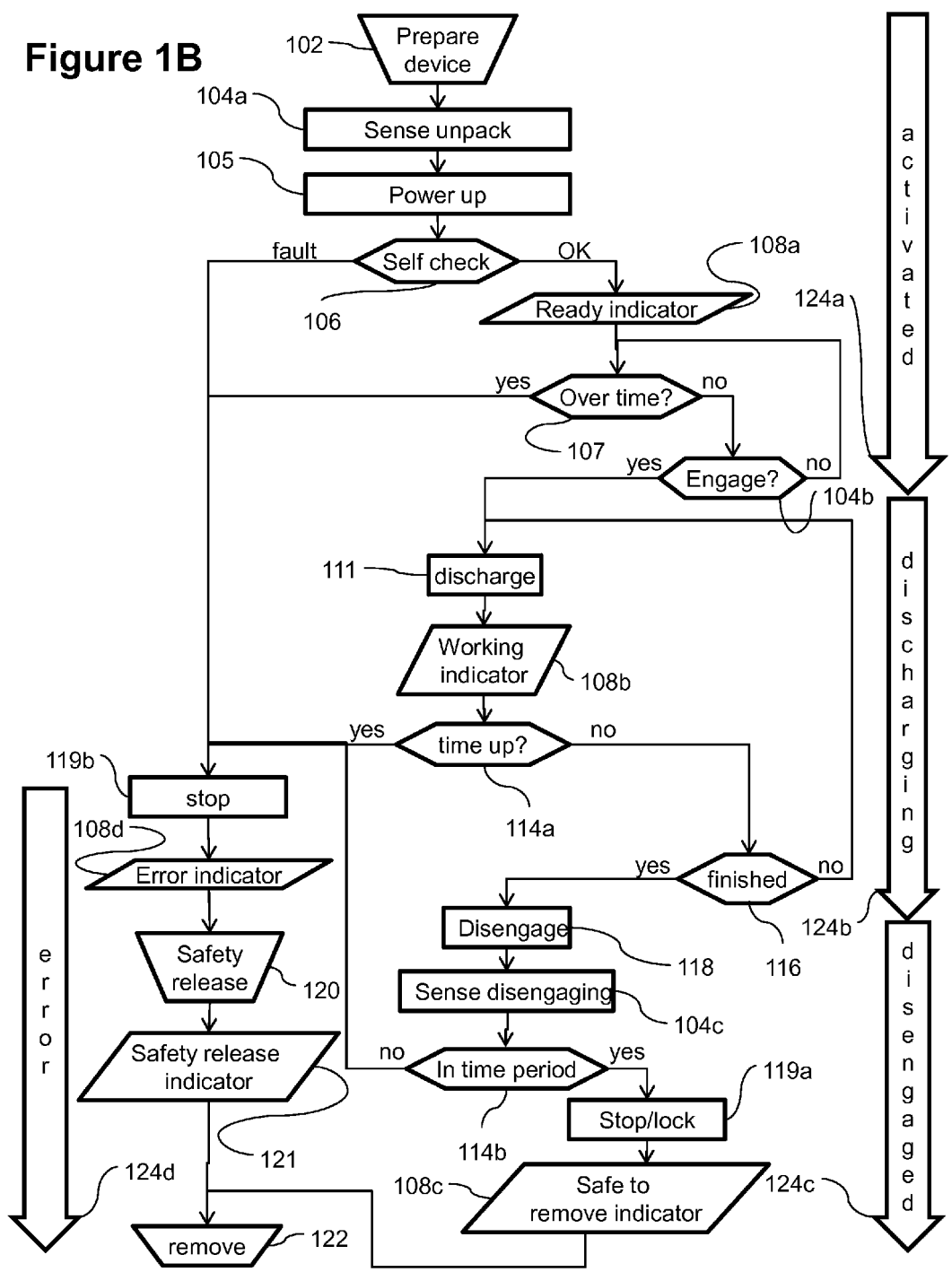

FIG. 1B illustrates a flow chart of a method of controlling a drug delivery device in accordance with an embodiment of the current invention. In some embodiments a drug delivery device the device may include diagnostic tests. The results of the diagnostic tests may be used to determine when to switch between modes and/or to the results of the diagnostic tests may be indicated to a user for example through a coded indicator.

In some embodiments, when a device is activated 105, the device runs a self check 106. Self check 106 may include, for example, checking a battery condition and/or a motor condition and/or checking the position of a plunger and/or a telescoping element and/or the syringe position and/or checking a flag, for example a Not-activated flag in the software and/or running check sum to verify that a software is OK. If the self check comes out OK, then the device will optionally indicate 108b that it is ready for engagement to a subject. If there is a fault in self check 106, then the injector optionally goes into an error state 124d.

In some embodiments, there will be a time check for certain actions. For example after the indicating 108b that the device is ready the system may wait for the user to engage 110 the device to a subject. Optionally, the system will keep checking the time 107 and sensing 104a whether the device is engaged 110. If the time 107 period ends without engagement 110, then the system optionally goes to an error state 124d and/or indicates 108d that an error has occurred. If the device senses 104a engagement 110 before the end of the time period, then the system optionally enters discharge stage 124b. For example, for a system where a user is given an inactivated device and/or activates the device before use, the engaging wait time before indicating 108d an error may range between 30 sec. to 2 minutes and/or between 2 to 5 min and/or between 5 to 10 minutes and/or between 10 and 30 minutes. Alternatively or additionally a device may have a programmable engaging timer. For example, a device may be made to be given to a user by a medical professional in an activated state. The device may wait a certain time period (for example ranging from one hour to 6 hours and/or from 6 hours to two days) and alert the user that the time to take his medicine has come (for example via a light indicator and/or an audio alarm and/or a cellular message). Then the device may optionally wait to be engaged. For example the device may wait a time period ranging between 30 sec. to 2 minutes and/or between 2 to 5 min and/or between 5 to 10 minutes and/or between 10 and 30 minutes and/or between 30 minutes to two hours. If the device is not engaged by the end of the wait period it may indicate an error.

In some embodiments, an error indicator may include a coded message associated with the device. For example, a LED may glow red and/or blink red. Alternatively or additionally, there may be an auditory indicator and/or a cellular message may be sent. For example the message may be sent to the user and/or to a supervisor and/or a medical professional. The cellular message is optionally different details from the message associated with the device. For example the message to a user may "say fault consult your doctor" whereas the message to a doctor may have details of the error (whether any medicine was administered, how long and what time did the error occur etc.).

In some embodiments, when a fault occurs and/or when the device has successfully completed operation, the device may be locked to prevent use of the device against instructions. Alternatively or additionally there may be a warning period and/or a warning indicator. If corrective action is not taken during the warning period the device may be locked. Alternatively or additionally, the device may remain usable when an error occurs and/or may lock due to certain errors and remain usable when there are other errors. Locking may be permanent and/or reversible (reversing the locking may be available to the user and/or only to a medical professional). For example, for a device with an experienced user (for example an insulin pump) the indications and/or options for the user may be more complex and include more options and/or more reversibility. For example, for a device for inexperienced users and/or more limited users (for example an injector for use by cancer patient and/or geriatric patients) the errors may be stricter, the instructions simpler and/or the options more limited and/or the waiting times shorter. In some embodiments the device may have a reset switch to unlock the device. The reset switch may be hidden and/or protected from user activation. Alternatively the reset switch may be available to the user. For example, after the device is locked, activating the reset switch may be cause the device to return to the unactivated and/or initial and/or unlocked state. Optionally there may be a warning and/or time delay before returning to the unactivated and/or initial and/or unlocked state.

In some embodiments, discharge stage 124*b* may have a time limit. For example, if discharging does not finish 116 within a determined time up 114*a* period, the device may go into an error state 124*d*. For example, the device may go into an time out error if the motor is not properly connected to the plunger such the system may never discharge and/or discharge may never finish 116. Alternatively or additionally, if the system disengages before a determined minimum time period 114*b*, the system may go into error state 124*d*. For example, a sub-minimum time error may occur when there is a blockage in a fluid path and/or the resistance to movement of the plunger rises high enough to cause the system to prematurely disengage 118. The minimal discharge time period 114*b* and/or maximum time period 114*a* may vary, for example, according to the expected discharge time, the consequences of an under-dose, the consequences of a mistaken missed delivery, the level of supervision, the expected variability of the discharge time, the physical condition of the user, the mental condition of the user and/or the experience of the user (for example the likelihood to recognize and correct errors themselves). For example, the minimal discharge time period 114*b* may range between 0 to 20% of the expected time period and/or between 20 to 50% and/or between 50 to 80% of the expected discharge period. For example, the maximum time period 114*b* may range between 100 to 120% of the expected time period and/or between 120 to 150% and/or between 150 to 200% of the expected discharge period and/or between 200 to 500% of the expected discharge period. The expected time period for discharge may vary for example with the viscosity and/or volume of the drug. For high viscosity and/or high volume of drug the expected injection time may increase.

In some embodiments, during discharge stage 124*b* a plunger location sensor may track motor rotation and/or plunger position (for example with magnetic or optic sensors). Plunger location is optionally used to find if the injection process and plunger movement are according the program. In some embodiments, when plunger position deviates from a program by a sufficient amount, the device may enter an error state 124*d*.

In some embodiments, when the device enters an error state 124*d*, the system may be stopped 119*b*. For example, stopping in an error state 124*d* may include some or all of the options of stopping 119*a* after successful discharging 124*b*. In the error state 124*d* the user may trigger a safety release 120 and/or remove 122 the injector. Optionally, the triggering safety release retracts a needle and/or causes display of a safety release indicator 121. For example the safety release indicator 121 may indicate that it is safe to remove 122 the device (e.g. because the needle has been retracted) and/or that discharge 124*b* did not complete successfully and/or a supervisor should be consulted.

States of a Drug Delivery Device

Figure 2:
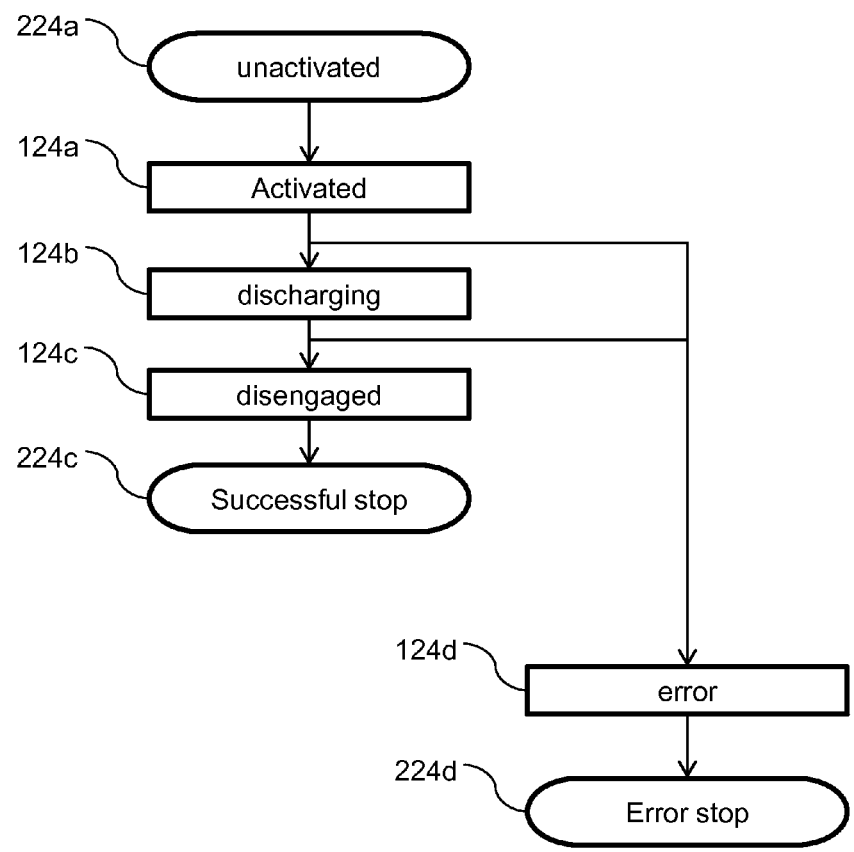
FIG. 2 is a state diagram illustrating states and/or stages of operation of a drug delivery device in accordance with an embodiment of the current invention.

FIG. 2 is a state diagram illustrating stages of operation of a drug delivery device in accordance with an embodiment of the current invention. In some embodiments a drug delivery device may have multiple stages of operation and/or states. A coded output device may indicate to a user the current stage of operation of the device. A sensor and/or a reusable power switch may be used to determine timing and/or order of changes of state of the device. Control of the device and/or user indicators may be according to the output of the sensor and/or reusable power switch.

Optionally, an active output device such as a light and/or a sound source may supply reassuring feedback when the device is functioning properly. An alternative indicator may inform the user of the status of delivery when the device is not active. For example, a passive sign and/or an optical path formed in the housing to view the reservoir and/or a state of the reservoir may make it possible as ascertain whether and/or how much medicine was discharged and/or whether the device was used and/or whether the device went through and error state.

In some embodiments a delivery device may have multiple stages of delivery. For example the device may have an activated stage 124*a* and/or a discharging stage 124*b* and/or a disengaged stage 124*c*. Each stage of delivery optionally has an active and/or coded and/or distinctive status indicator for reassuring a user that delivery is proceeding properly and/or to help the user determine in a very simple way what he needs to do. Alternatively or additionally a device may have an error state and/or an active and/or coded and/or distinctive error indicator.

In some embodiments a delivery device may have multiple inactive states. For example a device may have an unactivated and/or preliminary state 224*a* and/or a successful delivery stopped state 224*c* and/or and error stopped 224*d* state. Optionally some or all of the inactive states may have a passive indicator that allows a user and/or a supervisor (for example a medical professional and/or a caregiver) determines whether and/or how much medicine was discharged and/or whether delivery proceeded normally.

Schematic Diagrams of a Drug Delivery Device

Figure 3A:
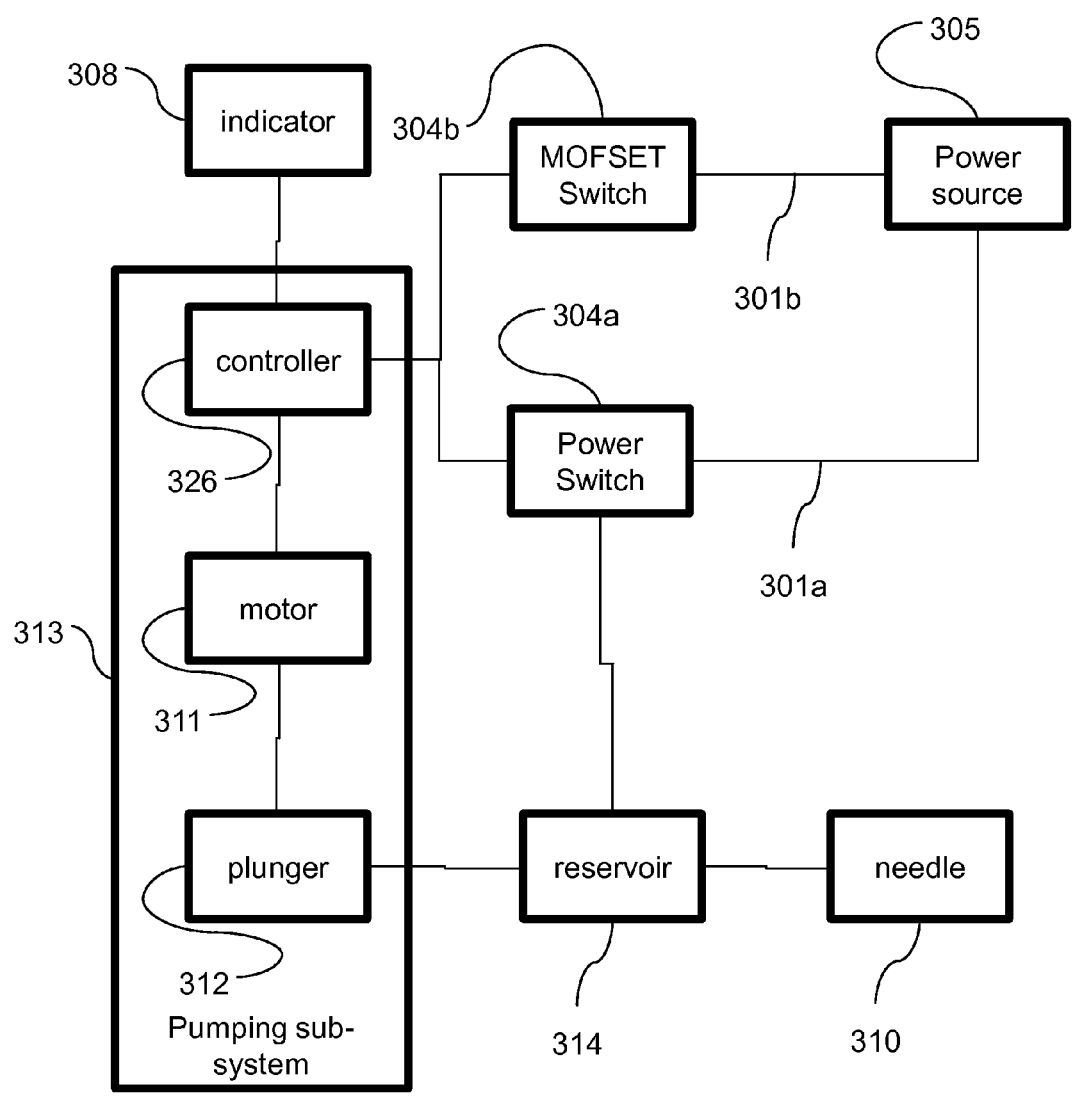
FIGS. 3A and 3B are block diagrams a drug delivery device in accordance with an embodiment of the current invention.
Figure 3B:
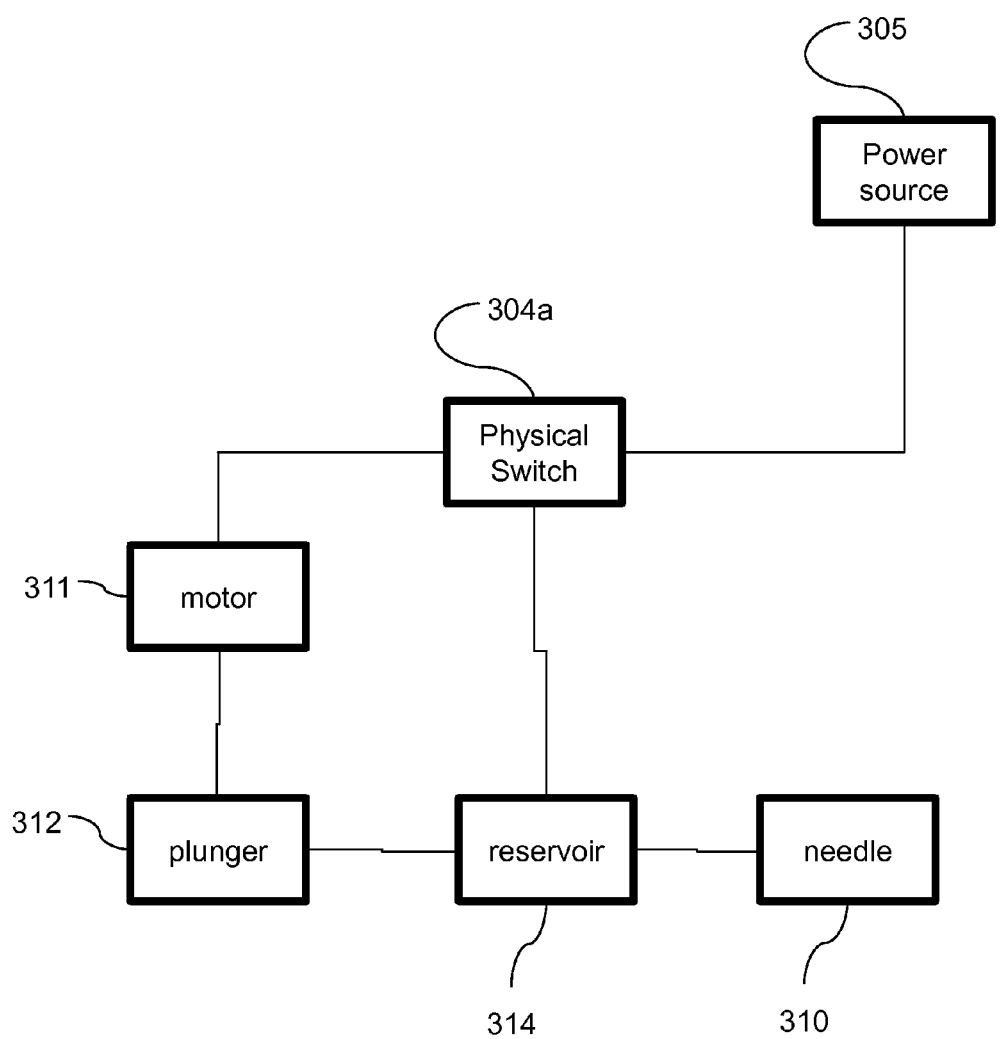

FIG. 3A is a block diagram a drug delivery device in accordance with an embodiment of the current invention. For example, the device may include multiple power circuits. For example a first power circuit 301*a* may be controlled by a power switch 304*a*. Power switch 304*a* may initially insolate a power source 305 from a pumping sub-system 313 and/or an indicator 308. In some embodiments, power switch 304*a* may be toggled to activate the device by a user action (for example unpacking the device). After the system is activated, power switch 304*a* may optionally function as a sensor for determining a stage and/or state of the device. For example, power switch 304*a* may be toggled by movements of a needle and/or a reservoir of the device.

In some embodiments, after the system is activated, a processor 326 may control various components of the system. For example, processor 326 may send commands to indicator 308. For example, indicator 308 may indicate a stage and/or status of the device to a user via coded output. Optionally, processor 326 may control discharge of a drug. For example, when a needle is engaged to a subject, processor 326 may send commands and/or power (for example electrical current) to a motor 311 driving a plunger 312 to discharge the drug from a reservoir 314 through the needle 310 into the subject.

In some embodiments, a second power circuit 301*b* may be controlled by a MOFSET switch 304*b*. MOFSET switch 304*b* may initially insolate power source 305 from a pumping sub-system 313 and/or indicator 308. When, the system is activated, the gate of MOFSET switch 304*b* is optionally opened by a voltage potential supplied through the first power circuit and/or via processor 326.

In some embodiments, after activation of the system, processor 326 may be responsive to signals from a sensor. Optionally, after activation, power switch 304*a* may be toggled by actions of the device while processor 326 receives power over circuit 301*b*. For example, power switch 304*a* may be toggled by movements of reservoir 314 and/or needle 310. Optionally, processor 326 may track the state of the device and/or issue commands based on the order and/or timing of toggling of switch 304*a* and/or based on the status of switch 304*a* and/or other sensors. In some embodiments, reusing a switch for multiple indications may reduce the number of sensors in the device. Reducing the number of sensors optionally reduces cost of the device and/or reduces the size of the device.

FIG. 3A is a block diagram a drug delivery device in accordance with an alternative embodiment of the current invention. In some embodiments, control of various subsystems may be based on direct connections to one or more sensors. Optionally the device may lack a central processor.

In some embodiments, motor 311 and/or output device 308 may be directly connected to a power switch. For example, when needle 310 is engaged to a subject, switch 304 is toggled on and/or motor 311 is optionally turned on and/or output device 308 is activated producing a working indicator. Optionally, motor 311 drives a plunger 312 discharging a drug. When needle 310 is disengaged from the subject, switch 304 is optionally toggled off and/or motor 311 is optionally turned off, stopping discharge of the drug and/or output device is turned off and/or switched to produce a second coded indication. For example the second coded indication may indicate that delivery has finished and/or that it is safe to remove the delivery device.

Power Switch Sensing User Actions

Figure 4A:
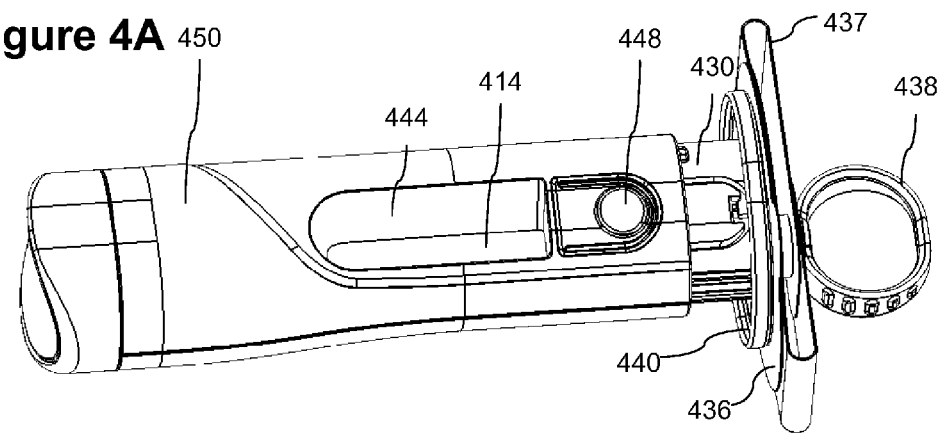

FIG. 4A is a perspective view of a multistage drug delivery device in an unactivated state in accordance with an embodiment of the current invention. In some embodiments, a power switch 403*a* and/or another switch 403*b* (for example see FIG. 4M) are repeatedly toggled by various components of the system as the system proceeds. The order and timing of the toggling are optionally used to distinguish and/or control stages of operation of the device and/or or to control a status indicator of the device. For example in the unactivated state, power switch 403*a* isolates a power supply 405 from the power consuming components of the device.

FIG. 4A is a perspective external view of a multistage drug delivery device in an unactivated state in accordance with an embodiment of the current invention. In some embodiments, pulling away a handle 438 and/or a protective cover 437 toggles a power switch 403*a* and/or activates the device. Handle 438 is optionally connected to protective cover 437. In some embodiments, a drug reservoir 414 is optionally visible through a window 444 in a housing 450 of the device. Optionally, in the unactivated state, reservoir 414 is not illuminated. For example, before activating the device a user and/or a supervisor may be able to look into the reservoir and determine the state of the contents; for example if the reservoir is properly filled, if the contents are the proper color etc.

Figure 4B:
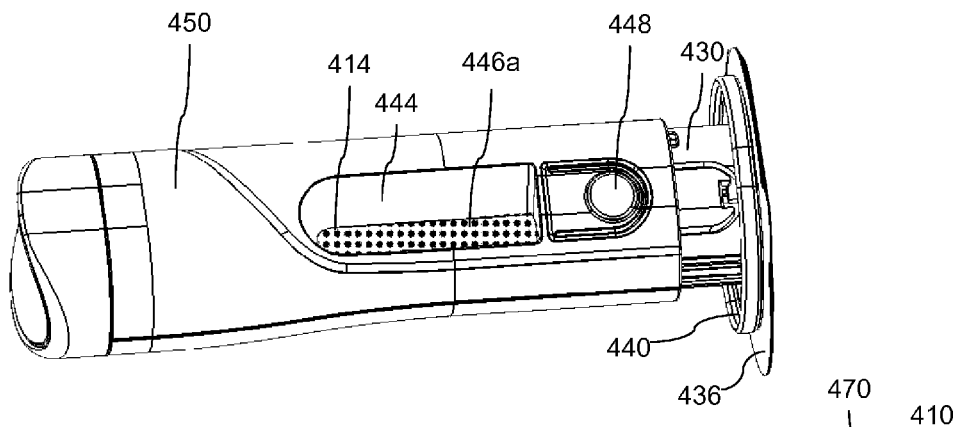

FIG. 4B is a perspective view of a drug delivery device in an activated state in accordance with an embodiment of the current invention. For example, handle 438 and/or protective cover 437 have been pulled away activating the device. Optionally, removing cover 437 uncovers an adhesive layer 436 covering and/or a skin contact member 440. For example, in the activated state, skin contact member 440 may be extended by a sleeve 430 past a needle tip. In some embodiments, in the activated state, reservoir 414 and/or window 444 are illuminated by a coded activated indicator light 446*a* (represented in FIG. 4B by the diamonds visible in window 444). For example, the activated stage indicator light 446*a* may be a constant blue illumination of the reservoir. Optionally, indicator light 446*a* may be more obvious than the physical state of reservoir 414 and/or may obscure the physical state of reservoir 414. For example, when a user (who may be inexperienced) looks window 444 during the activated stage, he sees the obvious blue light.

Figure 4C:
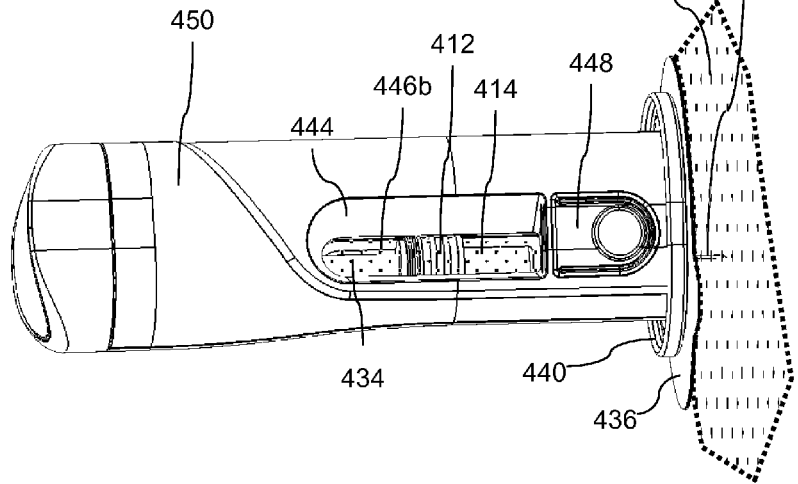

FIG. 4C is a perspective view of a drug delivery device in a discharging state in accordance with an embodiment of the current invention. For example, while the device is in the activated state, a user pushes skin contact member 440 against the skin 470 of a subject. Pressure optionally collapses sleeve 430 and/or shortening housing 450. Optionally, shortening housing 450 exposes the tip of needle 410. For example, needle 410 may penetrate the skin 470 of a subject. A sensor (for example the power switch of the device) optionally senses the collapse of sleeve 430. In some embodiments, in response to sensor output, a motor may start to drive a plunger 412 and/or to discharge the drug and/or a coded discharging indicator may be initiated. In the discharging state a user may optionally see plunger 412 as it passes along reservoir 414. In some embodiments, in the activated state, reservoir 414 and/or window 444 are illuminated by coded activated indicator light 446*b*. For example, the discharging stage indicator light 446*b* may be a blinking green illumination of the reservoir. Optionally, indicator light 446*b* may be more obvious than the physical state of reservoir 414 and/or may obscure the physical state of reservoir 414. For example, when a user (who may be inexperienced) looks window 444 during the discharging stage, he sees that obvious green blinking light. In some embodiments, indicator light 446*b* may reassure the user that the device is operating properly and/or will avoid the user getting confused trying to understand the state of the device from the appearance of reservoir 414.

Figure 4D:
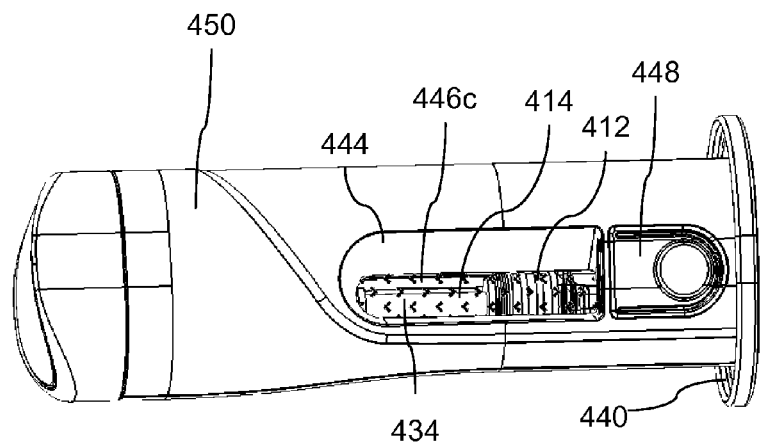

FIG. 4D is a perspective view of a drug delivery device in a stopped state in accordance with an embodiment of the current invention. For example, after successful drug delivery, needle 410 has been retracted into housing 450. In some embodiments, after successful delivery, reservoir 414 is illuminated by a coded activated indicator light 446*c*. For example, after successful delivery indicator light 446*c* may be a constant green illumination of reservoir 414 and/or window 444. In some embodiments, once needle 410 has been retracted a user may remove the device from the subject. After delivery and/or in the stopped state drug reservoir 414 is visible through a window 444. Optionally, from the appearance of the reservoir it is possible to see the inside of the reservoir. For example, in FIG. 4C, plunger 412 is shown having moved all the way to the distal end of reservoir 414 indicating that all of the drug has been discharged. The reservoir optionally remains visible whether or not indicator 446*a*-446*d* is lit. For example, the user and/or a supervisor who can see whether the discharge completed whether or not the electrical system of the device is working (for example after the power supply has been exhausted).

Figure 4E:
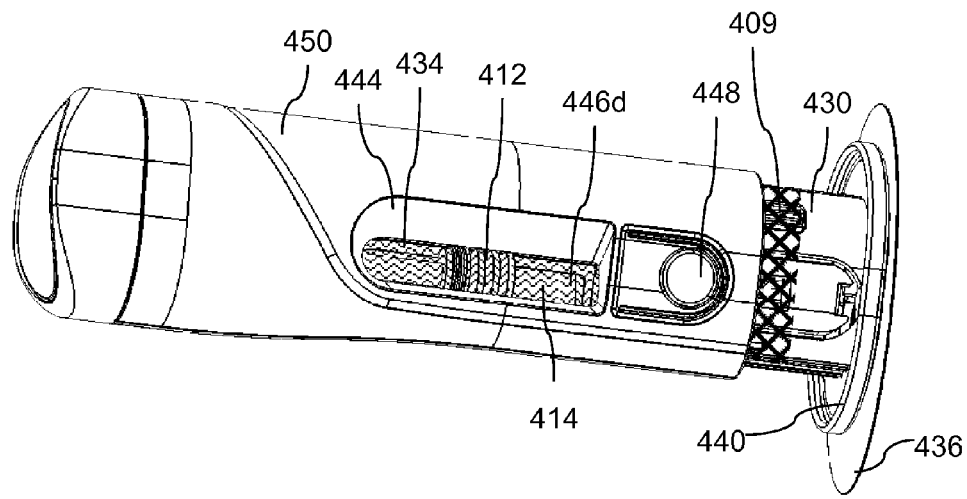

FIG. 4E is a perspective view of a drug delivery device in an error state after safety release in accordance with an embodiment of the current invention. For example, when an error occurs after activation of the device, an error indicator 446*d* (for example a red light) may be displayed. Optionally, upon seeing error indicator 446*d* a user pushes a safety release button 448. Optionally, safety release button 448 releases sleeve 430 and/or skin contact member 440 to extend outward past needle 410. For example extending sleeve 430 may retract needle 410 from the subject to behind skin contact member 440. Extension of sleeve 430 in the safety release state (for example as illustrated in FIG. 4E) is optionally further than extension in the activated state (for example as illustrated in FIG. 4B). An indicator strip 409 may be visible after safety release. For example indicator strip 409 may indicate that the safety release has been activated and/or that discharge may have been aborted and/or that needle 410 has been retracted by the safety release and/or that the device may be safely removed from the subject. For example, in FIG. 4C, plunger 412 is visible through window 444. Plunger 412 is still located near the middle of reservoir 414 indicating that not all of the drug has been discharged. The reservoir optionally remains visible whether or not indicator 446a-446d is lit. For example, the user and/or a supervisor who can see whether the discharge completed whether or not the electrical system of the device is working (for example after the power supply has been exhausted).

Figure 4F:
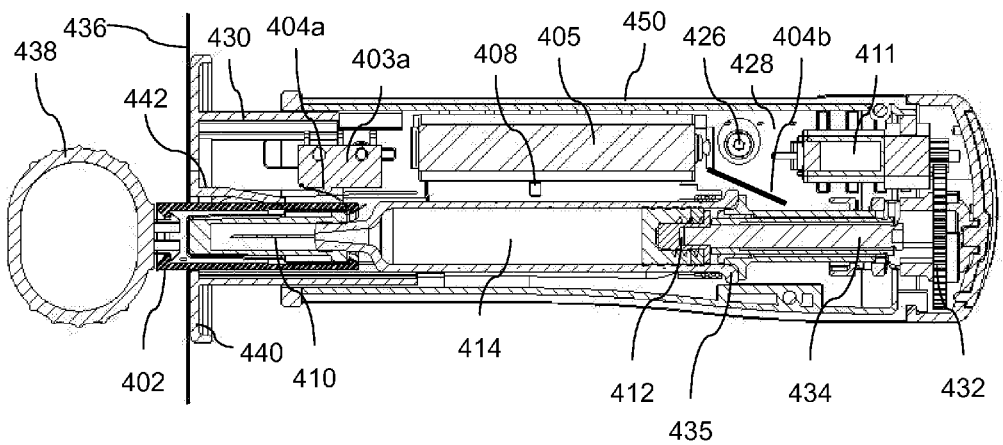

FIG. 4F is a cutaway viewing illustrating internal parts of a drug delivery device in an unactivated state in accordance with an embodiment of the current invention. In some embodiments, a drug delivery device may include two sensor switches 403a and 403b. Optionally each switch 403a and 403b includes a respective sensor arm 404a and 404b. In the unactivated state, power source 405 (for example a battery) is optionally isolated from the active components of the system (for example a motor 411 and/or a processor 426 and/or an output device, for example LED 408). For example, in the embodiment of FIG. 4F, power source 405 is optionally isolated from the active components of the system by power switch 403a which is in a disconnect configuration. Switch 403a optionally remains in the disconnect configuration as long as sensor arm 404a is deflected towards the body of switch 403a. In some embodiments, in the unactivated state and/or while sensor arm 404a remains deflected towards the body of switch 403a, substantially no power is drained from power source 405 and/or the delivery device consumes substantially no power. In some embodiments, sensor arm 404a may be held deflected toward the body of switch 403a by a protective needle cover 402.

In some embodiments, switches 403a-403b may sense movements ranging between of 1 to 4 mm. For example arm 404a and/or 404b may include a flexible element and/or may bend. In some embodiments switches 403a-403b movement of arm 404a and/or 404b may range between 4 mm to 10 mm. Activation force for the switch may range for example between 20 to 100 gr. Switch dimensions may range between 5 to 9 mm but can be smaller or bigger.

Figure 4G:
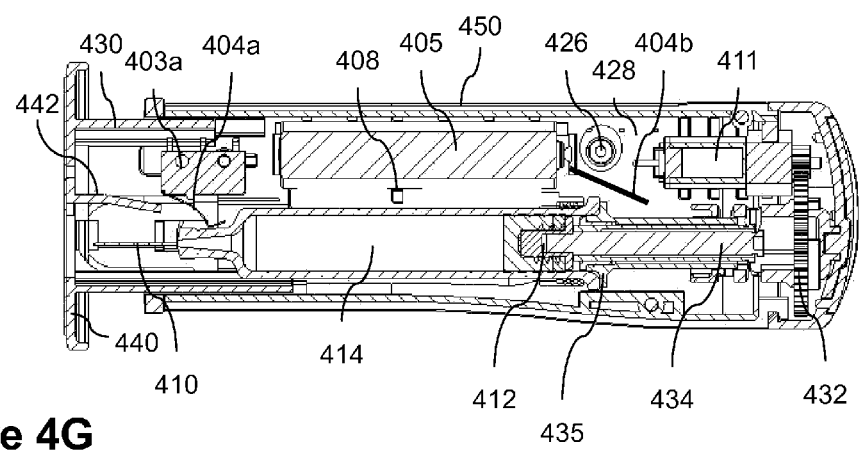

FIG. 4G is a cutaway view illustrating internal parts of a drug delivery device in an activated state in accordance with an embodiment of the current invention. Optionally, switch 403a is toggled to a connecting state and/or connects power source 405 to processor 426. For example, switch 403a is toggled to a connecting state when a user removes a protective cover 402. Particularly, in some embodiments, when cover 402 is removed sensor arm 404a is released and/or moves away from switch 403a, toggling switch 403a to the connected configuration.

In some embodiments, when processor 426 is powered up from the unactivated state, processor 426 performs a device self test and/or activates a second power circuit. If the self test is successful, processor 426 connects LED 408 to power source 405 and/or commands LED 408 to indicate that the device is activated and/or ready for engagement.

Figure 4H:
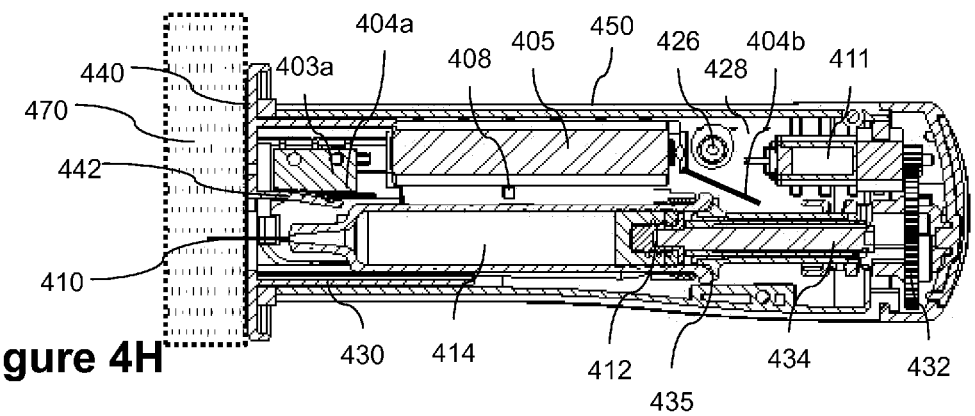

FIG. 4H is a cutaway viewing illustrating internal parts of a drug delivery device in an engaged and/or discharging state in accordance with an embodiment of the current invention. Optionally, switch 403a is toggled when the device is engaged to a subject; for example when needle 410 extends into skin 470 of the subject. When the device in the activated state, the device may respond to toggling of switch 403a by entering a discharge state. Entering a discharge state may include for example initiating discharge of the drug and/or indicating that discharge has started (for example via a coded indicator from LED 408).

In some embodiments, switch 403a may be toggled by movement of skin contact member 440 with respect to housing 450. For example, a user may hold housing 450 and/or press skin contact member 440 against skin 470 of a subject until sleeve 430 collapses and/or slides into housing 450. Optionally as sleeve 430 moves with respect to housing 450, it contacts arm 404a and/or toggles switch 403a. For example as sleeve 430 collapses a portion 442 of contact member 440 presses against arm 404a toggling switch 403a. As sleeve 430 slides into housing 450, needle 410 is optionally exposed and/or inserted into skin 470. Optionally, after the activated stage, when switch 403a is toggled to a disconnect state, the second power circuit continues to supply power from power source 405 to processor 426 and/or other elements of the device. Optionally, processor 426 may include a timer and/or a real time clock. In some embodiments, processor 426 may track elapsed time between events and/or issue alerts and/or error messages and/or place the device into an error state when an expected event does not occur in the proper time period and/or when events occur in an improper time period.

In some embodiments, discharge may be driven by a motor 411. For example, motor 411 may drive a transmission 432. Optionally transmission 432 drives an telescoping screw 434 and/or plunger 412.

Figure 4I:
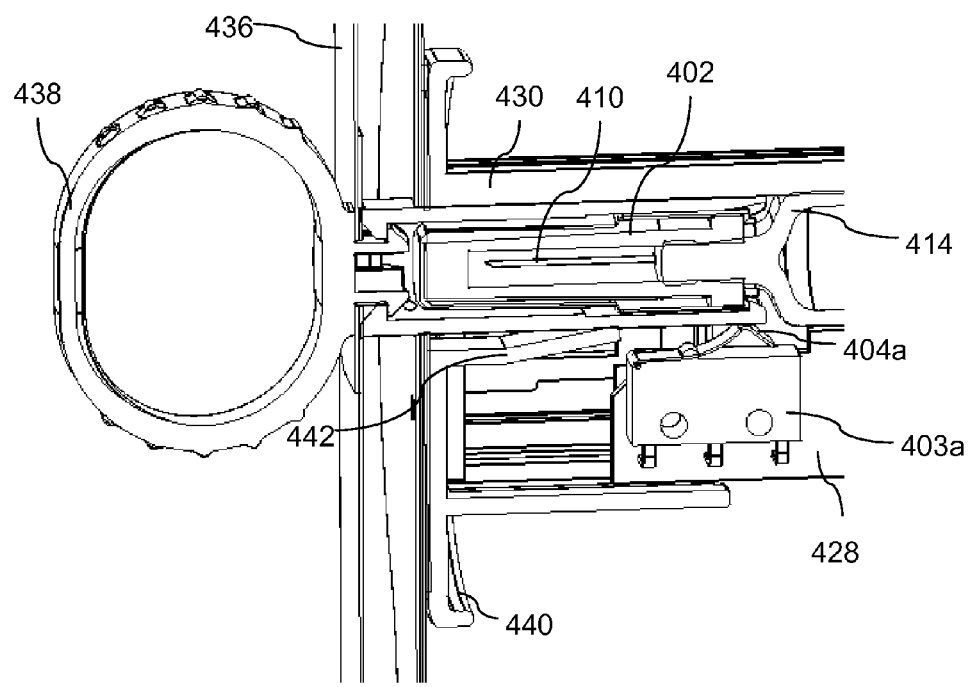

FIG. 4I is a close up cutaway perspective view illustrating internal parts of a drug delivery device in an unactivated state in accordance with an embodiment of the current invention. Optionally, switch 403a includes spring metal ribbon sensor arm 404a. In some embodiments, in the unactivated state, arm 404a is deflected towards the body of switch 403a by cover 402. Optionally, deflecting arm 404a towards switch body 403a puts switch 403a into a disconnecting state. Optionally, in the unactivated configuration, in the disconnected state, switch 403a isolates power source 405 from processor 426.

FIG. 4J is a close up cutaway perspective view illustrating internal parts of a drug delivery device in an activated state in accordance with an embodiment of the current invention. In some embodiments, in the activated state, cap 402 has been removed. For example, without cap 402, arm 404a is free to move away from the body of switch 403a. Optionally, arm 404a moving away from body 403a puts switch 403a into a connecting state. Optionally, in the activated configuration, switch 403a conducts electricity between power source 405 and processor 426.

FIG. 4K is a close up cutaway perspective view illustrating internal parts of a drug delivery device in an engaged and/or discharging state in accordance with an embodiment of the current invention. In some embodiments, the device is engaged to a subject by pushing skin contact member 440 against the skin of a subject and/or by collapsing skin contact member 440 towards housing 450. Optionally, sensor 403a is mounted to a printed circuit board 428 which is stationary with respect to housing 450. Optionally, reservoir 414 and/or needle 410 are held stationary with respect to housing 450 by a supporting sleeve 435 (for example as illustrated in FIGS. 4F-4H). In some embodiments, as sleeve 430 and/or skin contact member 440 collapse towards housing 450, needle 410 moves with respect to skin contact member 440 and/or extends out from skin contact member 440 into skin 470 of the subject. In some embodiments, as sleeve 430 and/or skin contact member 440 collapse towards housing 450, they push arm 404*a* towards sensor body 403*a*. Pushing arm 404*a* toward sensor body 403*a* toggles switch 403*a* to disconnect the first power circuit. Optionally processor 426 detects the change in state of sensor 403*a* and puts the device into discharging state. Optionally, processor 426 and/or other components of the device continue to receive power over the second power circuit.

Figure 4L:
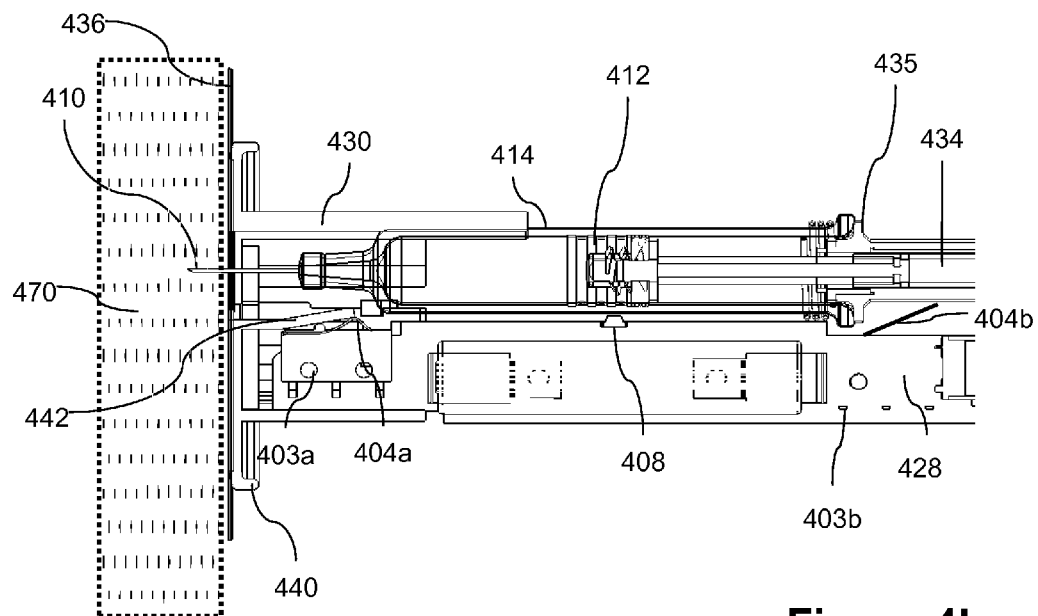
Figure 4M:
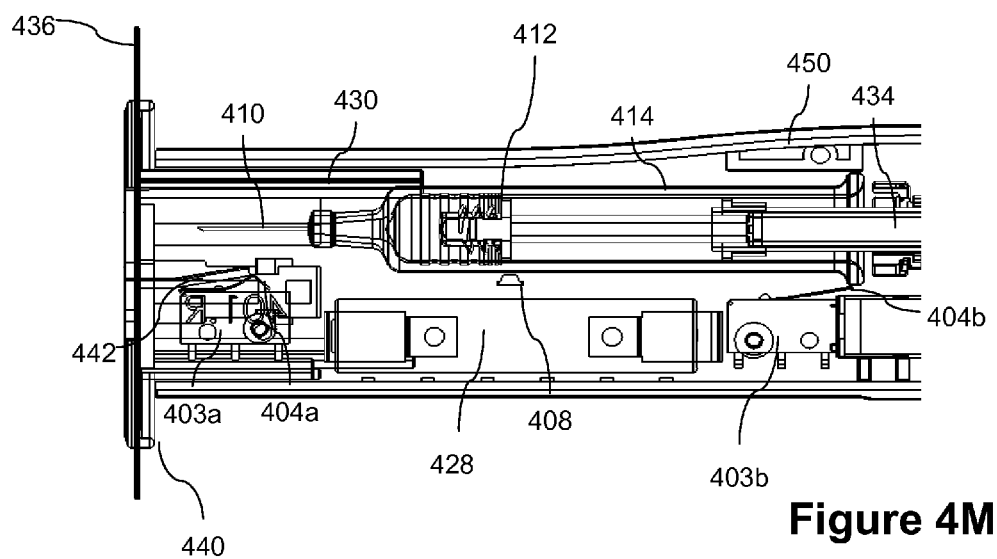

FIGS. 4L-4M illustrate toggling a switch by retraction of reservoir 414 and/or needle 410 in accordance with an embodiment of the current invention. In some embodiments, a drug distribution device may have two sensors 403*a*-403*b*. For example, the first sensor 403*a* may be used as a power switch and/or to sense user actions for example including unpacking the device (for example by removing a cover) and/or engaging the device to a subject and/or emergency disengagement. In some embodiments, first sensor 403*a* may be toggled by movement of, for example, a protective cover 402 and/or a skin contact member 440 with respect to needle 410 and/or with respect to housing 450, for example as illustrated in FIGS. 4A-4K. The second sensor 403*b* may be toggled by movement of the needle 410 and/or reservoir 414 with respect to the housing of the device.

In some embodiments, second sensor arm 404*b* is distanced from second switch 403*b* before and/or during operation of a drug delivery device (for example in the engaged state as illustrated for example in FIG. 4L). Optionally, when needle 410 and/or reservoir 414 are retracted, reservoir 414 pushes arm 404*b* towards switch 403*b* toggling switch 403*b*. Depending on the order of previous operations and/or timing thereof (for example as described in FIG. 1B and the accompanying description), processor 426 optionally responds to toggling of sensor 403*b* as a sign of premature end to delivery and/or successful completion of delivery. Optionally processor 426 responds to toggling of sensor 403*b* by activating an appropriate state indicator and or by starting or stopping an appropriate device (for example stopping discharge and/or locking the injector).

In some embodiments, according to the order and/or timing toggling of first and/or second switches 403*a*-403*b*, the device differentiates between premature retraction (for example due to obstruction of a fluid path) and retraction at the end of delivery (as illustrated for example in FIG. 4M, where plunger 412 has reached the end of reservoir 414 and/or discharged the entire contents of reservoir 414). For example if the delay between the beginning of discharge and toggling switch 403*b* is less than 95% of the expected delivery time and/or less than 85% of the expected delivery time and/or less than 70% of the expected delivery time, it may be assumed that discharge did not go to completion. If the delay ranges for example between 80% to 120% and/or between 50% and 200% and/or between 25% and 400% then the discharging may be assumed to have gone to completion. Alternatively or additionally, it may be assumed that injection didn't go to completion when the time between the beginning of discharge and toggling switch 403*b* is less than 95% of the minimum expected delivery time and/or less than 85% of the minimum expected delivery time and/or less than 70% of the minimum expected delivery time. Alternatively or additionally, an error may be indicated if the delay ranges for example greater than 105% and greater than 110% and/or greater than 120% and/or greater than 200% and/or greater than 400% of the maximum expected delivery time.

In some embodiments, a sensor may detect injection volume and/or plunger movement. In some embodiments, when the injection volume and/or plunger movement is less than a value validated as full dose, an error state and/or alarm may be set. When sensor toggling is on time and/or with plunger travel is within the expected range the process continues without error. Injection volume and/or plunger position and/or timing are optionally used together. For example when plunger movement is faster and/or slower than a prescribed value, an error state may be entered.

In some embodiments, according to the order and/or timing toggling of first and/or second switches 403*a*-403*b*, the device differentiates between retraction due to a user releasing a safety release (for example as illustrated in FIG. 4E and automatic retraction and retraction for example as illustrated in FIG. 4M (for example automatic retraction may be due to completion of delivery and/or a obstruction of a fluid path). For example, during automatic retraction reservoir 414 may toggle sensor 403*b* without affecting sensor 403*a*; whereas safety release from an engaged state (caused for example by a user pushing safety release button 448) may cause extension of skin contact element 440 toggling sensor 403*a* without affecting sensor 403*b*.

In some embodiments switch 403*b* may be used during a self check. For example at startup if switch 403*b* is not in the proper starting position than an error may be indicated and/or an error state entered. For example, if second sensor arm 404*b* is pushed towards sensor body 403*b* at start up, then it may be a sign that reservoir 414 is not in the proper position.

In some embodiments the device of FIGS. 4A-4M operates according to the methodology of FIGS. 1A-1B.

Power Switch Sensing Needle Movements

Figure 5A:
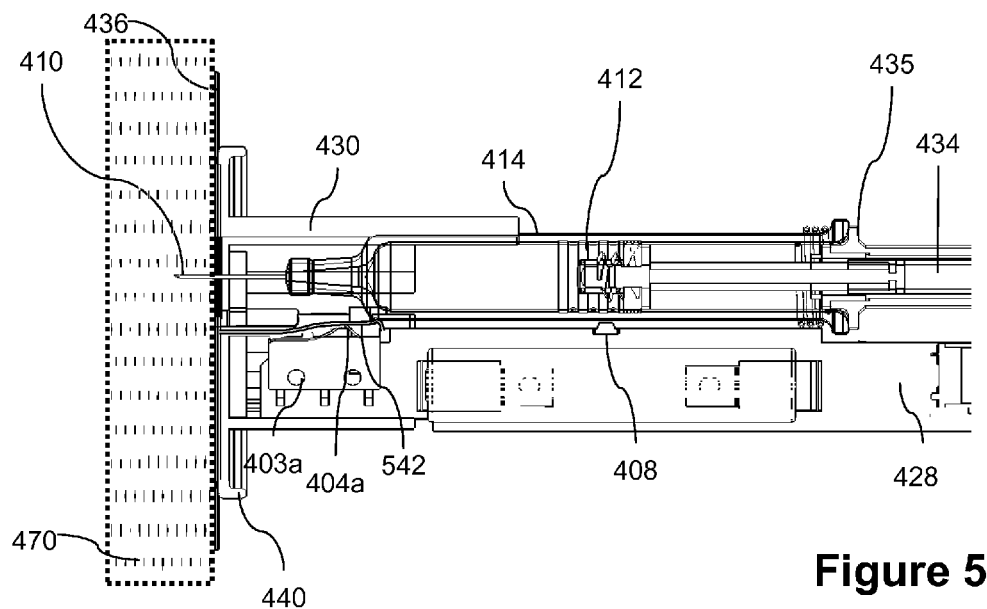
FIGS. 5A-5B are various views of a drug delivery device having power switch sensor in accordance with an embodiment of the current invention.
Figure 5B:
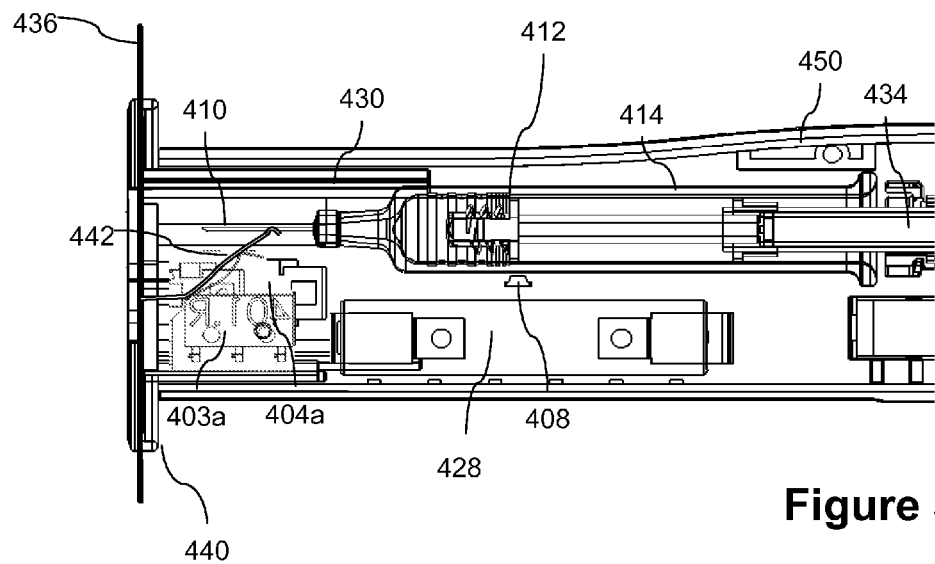

FIGS. 5A-5B are various views of a drug delivery device in which a single power switch serves to activate a device and/or sense engaging of the device and/or sense refraction of a needle in accordance with an embodiment of the current invention. In some embodiments, a flexible portion 542 of skin contact member 440 toggles switch 403*a* when the device is engaged. For example as illustrated in FIG. 5A, in the engaged state flexible portion is sandwiched between reservoir 414 and sensor arm 404*a* and/or pushes sensor arm 404*a* toward switch 403*a*. When needle 410 and/or reservoir 414 are retracted (for example at the end of discharging as illustrated for example in FIG. 5B) flexible portion 542 and/or sensor arm 404*a* are released and/or switch 403*a* is toggled. Optionally in the embodiment of FIGS. 5A-5B, a processor differentiates between automatic release at the completion of discharge and other causes of retraction (for example automatic retraction due to obstruction of a flow path and/or manual refraction resulting from activation of a safety release) based on the timing of the toggling of sensor 403*a* and/or plunger position and/or the combination of plunger position over time by other means. For example if the delay between the beginning of discharge and toggling switch 403*b* is less than 80% of the expected delivery time and/or less than 50% of the expected delivery time and/or less than 25% of the expected delivery time, it may be assumed that discharge did not go to completion. If the delay ranges for example between 95% to 110% and/or between 85% and 120% and/or between 75% and 140% then the discharging may be assumed to have gone to completion. If the delay is greater than 105% and/or greater than 120% and/or greater than 150% it may be assumed that an error occurred. For cases where an accurate does measurement is available (for example a plunger position sensor) a measure dosage range for example between 97% to 105% and/or between 95% and 110% and/or between 90% and 120% then the discharging may be assumed to have gone to completion. Otherwise, it may be assumed that an error occurred.

As illustrated for example in FIGS. 5A-5B, a drug delivery device may be controlled using a single power switch 403a. Optionally the switch 403a of the device of FIGS. 5A-5B may be toggled by the removal of a safety cover and/or activate the device as illustrated for example in FIG. 4F-4G.

Figure 6A:
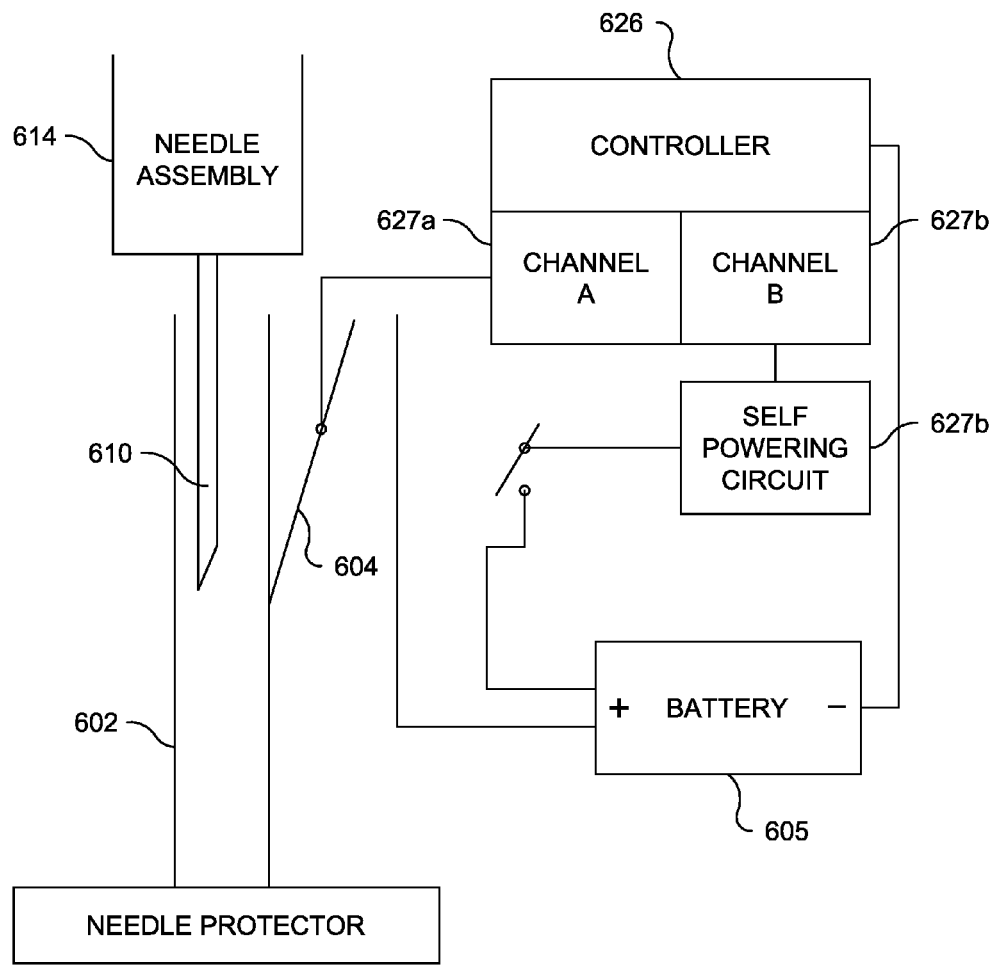
FIGS. 6A-6D are schematic views of a state sensing assembly in accordance with an embodiment of the current invention.
Figure 6B:
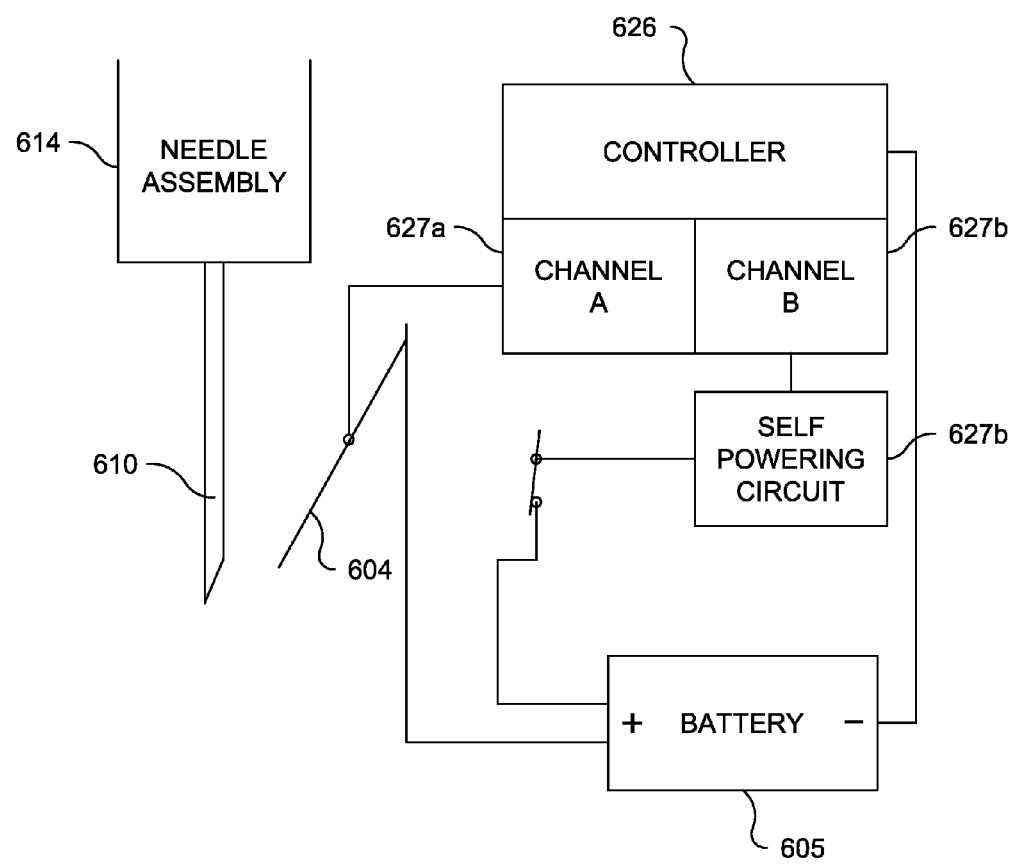

FIGS. 6A-6D are schematic views of a state sensing assembly in accordance with an embodiment of the current invention. In some embodiments, a simple mechanical switch 604 may be used in an unactivated state to isolate a power source 605 for example as illustrated in FIG. 6A. Switch 604 may be toggled to activate the device, for example as illustrated in FIG. 6B. Switch may be further toggled by movements of a needle 610 and/or a reservoir 614. For example, when the device is engaged (as illustrated for example in FIG. 6C) insertion of needle 610 into a subject may further toggle switch 604 and/or further toggling of switch 604 may initiate drug discharge and/or an indicator. For example, when the device is disengaged (as illustrated for example in FIG. 6D) retraction of needle 610 from the subject may again toggle switch 604 and/or again toggling of switch 604 may stop the device and/or initiate another indicator.

FIG. 6A illustrates a drug delivery device in an inactive state in accordance with an embodiment of the present invention. In some embodiments, removal of a protective cover 602 may toggle switch 604 to connect power source 605 to a controller 626 (for example as illustrated in FIG. 6B). Power may be supplied via switch 604 over a first power circuit 627a. Once activated, controller 626 optionally opens a self powering circuit (for example by opening a MOFSET switch) to supply power over a second power circuit 627b.

Figure 6C:
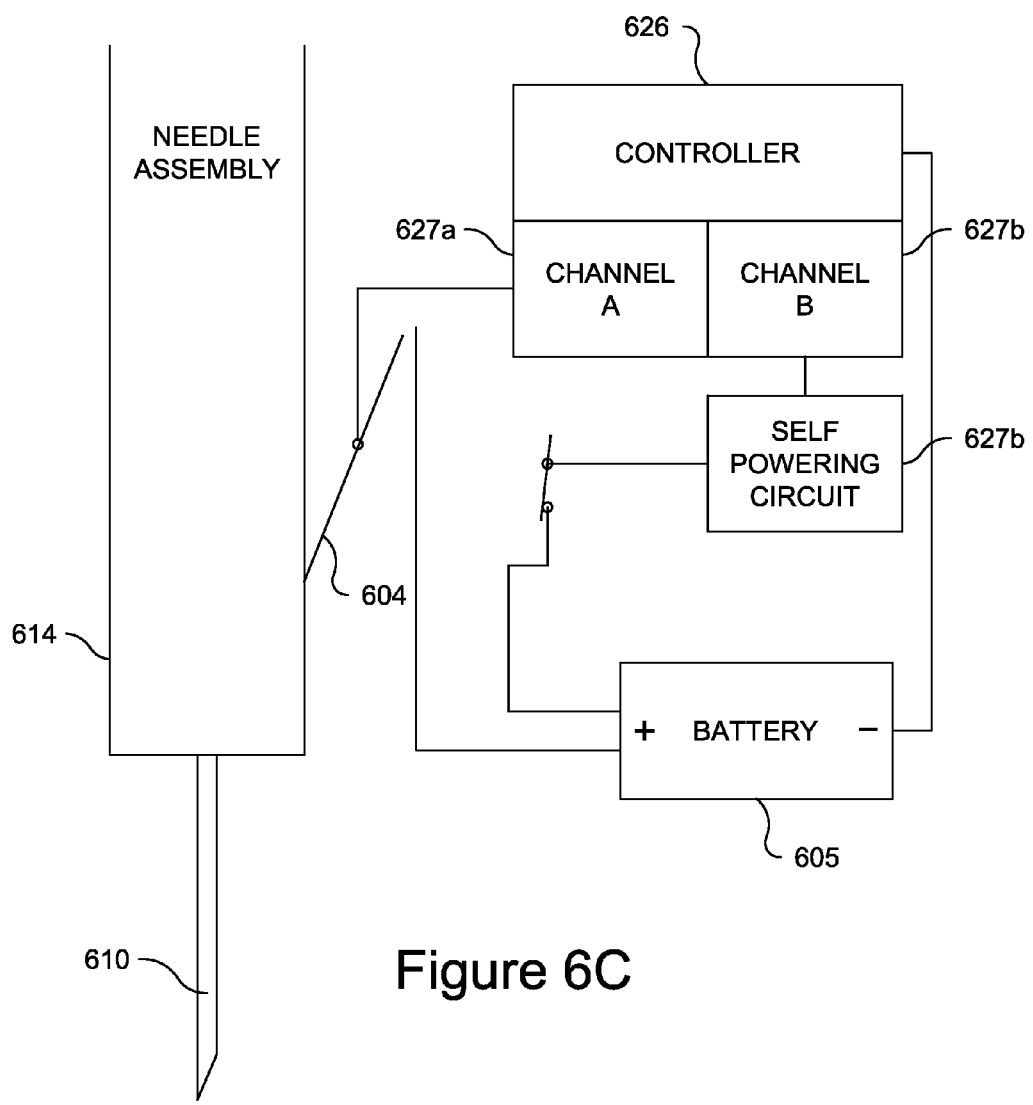
Figure 6D:
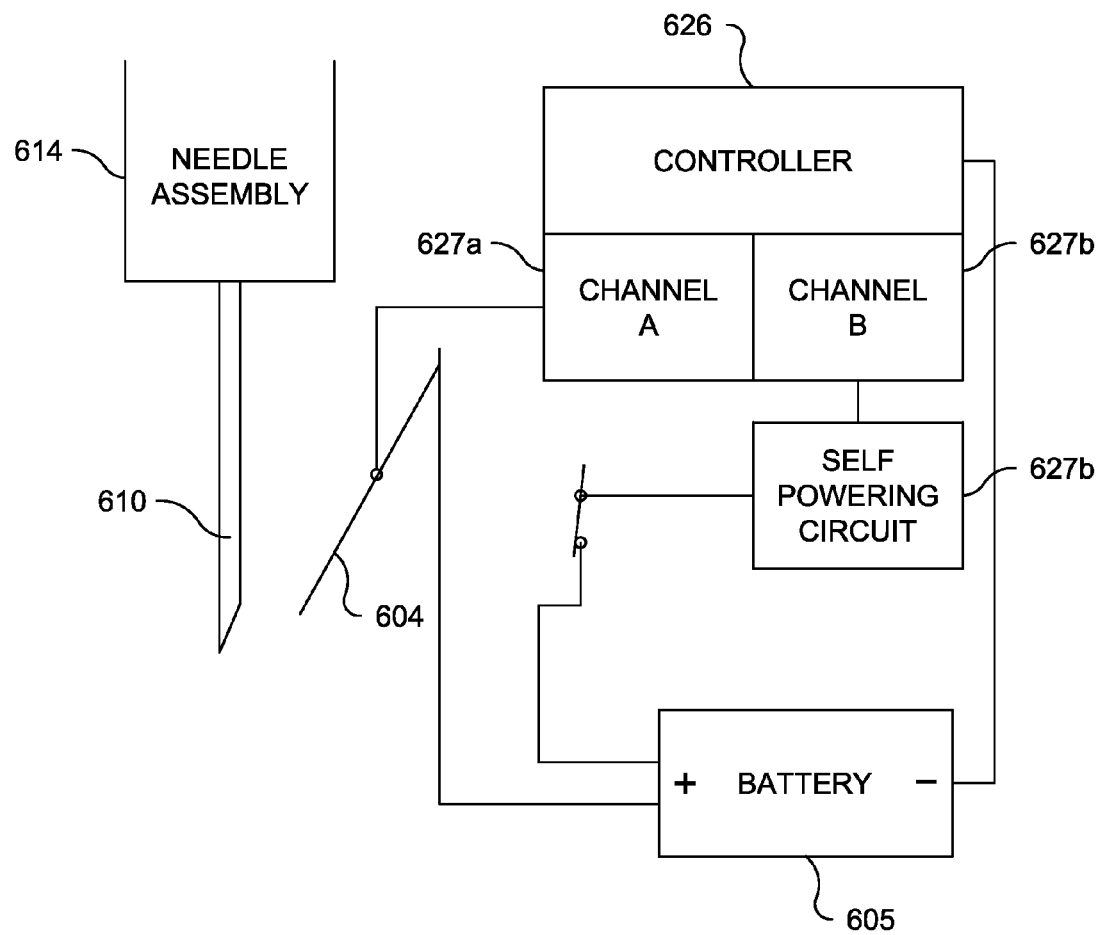

FIG. 6C illustrates a drug delivery device in an engaged and/or discharging state in accordance with an embodiment of the present invention. For example, extension of needle 610 may toggle switch 604 to a disconnect state. Optionally after activation, circuit 627b supplies power to controller 626 and/or switch 604 acts as a sensor of needle position. For example, extension of needle 610 toggles switch 604 to the disconnect state indicating to controller 626 that the system is in an engaged state. For example, retraction of needle 610 toggles switch 604 to the connect state (as illustrated for example in FIG. 6D) indicating to controller 626 that the system is in a disengaged state.

Exemplary Dimensions of a Drug Delivery Device

In some embodiments the payload of a reservoir (for example a syringe) may include, for example between 0.5 and 2 ml and/or between 2 and 4 ml and/or between 4 and 5 ml of a drug and/or more. In some embodiments, the injector may discharge the entire payload as a single dose. A drug delivery device may include, for example, a pen injector, and/or an internally powered driver to drive the plunger and/or discharge the payload. For the sake of this application an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example the driver may be designed to discharge the payload over a time period ranging between 20 and 120 seconds and/or between 120 and 600 seconds and/or longer. In some embodiments, discharge may be driven by a driver. An internally powered driver may be powered by various mechanisms including for example a motor (including for example a DC motor, an actuator, a brushless motor) and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the current invention may include reservoir. For example a reservoir may include a medicine container and/or a standard type syringe. Optionally a standard type syringe may be preloaded with medicine using standard equipment and/or in an aseptic room. A preloaded standard type syringe may optionally include a proximal opening. A plunger may optionally seal the proximal opening and/or protect the sterility of the contents of the syringe. A sterile needle (for example a hollow needle) may optionally be connected to the syringe barrel. For example, the hollow of the needle may be in fluid communication with the interior of the barrel. The needle may optionally be rigidly attached to the distal end of the barrel. The sterility of all and/or part of the needle may for example be protected by a sterile cover. The sterile cover may remain on the needle when the syringe is supplied and/or installed into an injector. For example, the medicine container may optionally include a cylindrical barrel rigidly attached to a needle. Optionally, the long axes of the needle and barrel of the syringe may be parallel and/or coaxial. Optionally, the needle may be mounted on the distal end of the barrel. Optionally the needle point may be pointing in the distal direction. In some embodiments a plunger may slide axially along the inside of the barrel to discharge a medicine payload. For example, the medicine may be discharged through the hollow needle.

An aspect ratio of the base may be defined as the ratio of the length of the longest axis of the base to the shortest axis. Optionally the axis ratio may range between 1 to 1.5 and/or 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N. Optionally, the force required to inject the drug (for example the force on a syringe plunger) may range for example between 5 to 60 N. For example the force required to inject the drug may depend on the injection rate and/or the viscosity of the drug and/or the syringe geometry and/or the needle dimensions.

In some embodiments a needle protection mechanism may be triggered by a linear force greater than, for example, between 10 to 60 N.

For example, drug delivery device may include an autoinjector. The autoinjector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example mechanism may include a snap that gives way at 40 N returning the needle to the refracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N*cm. The trigger torque (the torque at which the needle safeguarding is triggered) may range for example between to 0.5 to 2 and/or from 2 to 4 and/or from 4 to 10 N*cm.

In some embodiments a safety mechanism may include linear movement of the ranging between 5 to 15 mm. For example movement of the safety mechanism may include extension of a needle during insertion and/or retraction of the needle and/or extensions of a safety shield and/or retraction of a safety shield. Optionally a needle insertion length (for example the length of needle inserted into a patient) may range for example between 3 to 12 mm.

During injection, the linear movement of a plunger may range for example between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be refracted when the mechanism is exposed to a twisting moment. Optionally, discharge may be driven by a torque. For example the driver may apply torque to threaded element pushing a plunger. When the torque on the driver reaches a threshold value, the needle may be released and/or retracted and/or a needle shield may be deployed. Alternatively or additionally the trigger mechanism may require both a torque and a linear force. For example, requiring both a torque and a linear stress may prevent premature activation due to momentary friction.

In some embodiments a time of discharge may range may depend on the fill volume and/or viscosity For example the expected injection speeds may be Injection speed depend on viscosity, for example for viscosity ranging from 1 cp to 15 cp the expected injection rage may range between 30 to 40 sec/1 ml, for example for viscosity ranging from 15 cp to 60 cp the expected injection rate may range between 35 to 60 sec/ml for viscosity above 60 cp the expected injection rate may range between 53 to 67 sec/1 ml. The maximum and/or minimum expected injection time may for example be the maximum and/or minimum allowed fill volume divided by an injection rate. For example an expected time of discharge may range for example between 24 to 48 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 40 cp) and/or between 120 seconds and 3 minutes for larger volumes and/or viscosities It is expected that during the life of a patent maturing from this application many relevant technologies will be developed and the scope of the terms are intended to include all such new technologies a priori.

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A status sensor assembly for a multi-stage drug delivery device comprising:
   a first power supply circuit;
   a processor;
   a power switch isolating said first power supply circuit from said processor when the device is in an inactive stage and wherein in response to toggling of said power switch when the device is in said inactive stage said power supply circuit is connected to said processor, supplying power to said processor; said processor programmed to initiate an activated stage of the device in response to said supplying of power to the processor;
   a trigger assembly positioned to re-toggle said power switch upon engagement of the device to a subject;
   a sensor circuit indicating to said processor said re-toggling of said switch, said processor programmed to switch the device to a discharging stage in response to said indicating of said re-toggling;
   a driver responsive to said processor, said driver discharging the drug from the device when the device is in the discharge stage.

2. The assembly of claim 1, further comprising:
   a second power supply circuit, said second power supply circuit supplying no power to the processor when said device is in said inactive stage, said second power supply circuit responsive to said processor for supplying power to the processor in a discharging stage.

3. The assembly of claim 1, wherein in said inactive stage, substantially no power is supplied to said processor.

4. The assembly of claim 1, further comprising:
   a protective element, inhibiting engagement of the device to the subject, said protective element being connected to said power switch such that said toggling is performed by removing said protective element from the device.

* * * * *